US008183222B2

(12) United States Patent
Gilchrest et al.

(10) Patent No.: US 8,183,222 B2
(45) Date of Patent: May 22, 2012

(54) METHOD TO INHIBIT CELL GROWTH USING OLIGONUCLEOTIDES

(75) Inventors: Barbara A. Gilchrest, Boston, MA (US); Mark S. Eller, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 12/715,242

(22) Filed: Mar. 1, 2010

(65) Prior Publication Data

US 2010/0249218 A1    Sep. 30, 2010

Related U.S. Application Data

(63) Continuation of application No. 11/195,088, filed on Aug. 1, 2005, which is a continuation-in-part of application No. 10/122,630, filed on Apr. 12, 2002, now abandoned, which is a continuation-in-part of application No. PCT/US01/10162, filed on Mar. 30, 2001, which is a continuation-in-part of application No. 09/540,843, filed on Mar. 31, 2000, now Pat. No. 7,094,766, which is a continuation-in-part of application No. 08/952,697, filed on Nov. 30, 1998, now abandoned, which is a continuation-in-part of application No. 09/048,927, filed on Mar. 26, 1998, now Pat. No. 6,147,056, which is a continuation-in-part of application No. PCT/US96/08386, filed on Jun. 3, 1996, which is a continuation-in-part of application No. 08/467,012, filed on Jun. 6, 1995, now Pat. No. 5,955,059.

(51) Int. Cl.
*A61K 48/00* (2006.01)
*C07H 21/04* (2006.01)
*C07H 21/02* (2006.01)
*C12N 15/85* (2006.01)

(52) U.S. Cl. ... 514/44; 536/23.1; 536/24.31; 536/24.33; 536/24.5; 435/325

(58) Field of Classification Search .......... None
See application file for complete search history.

(56) References Cited

U.S. PATENT DOCUMENTS

| | | |
|---|---|---|
| 3,937,809 A | 2/1976 | Jacobi |
| 4,419,343 A | 12/1983 | Pauly |
| 4,508,703 A | 4/1985 | Redziniak et al. |
| 4,621,023 A | 11/1986 | Redziniak et al. |
| 5,077,211 A | 12/1991 | Yarosh |
| 5,256,648 A | 10/1993 | Gasparro et al. |
| 5,455,029 A | 10/1995 | Hartman et al. |
| 5,470,577 A | 11/1995 | Gilchrest et al. |
| 5,489,508 A | 2/1996 | West et al. |
| 5,532,001 A | 7/1996 | Gilchrest et al. |
| 5,580,547 A | 12/1996 | Gilchrest et al. |
| 5,583,016 A | 12/1996 | Villeponteau et al. |
| 5,585,479 A | 12/1996 | Hoke et al. |
| 5,599,672 A | 2/1997 | Liang et al. |
| 5,643,556 A | 7/1997 | Gilchrest et al. |
| 5,643,890 A | 7/1997 | Iversen et al. |
| 5,645,986 A | 7/1997 | West et al. |
| 5,686,306 A | 11/1997 | West et al. |
| 5,837,857 A | 11/1998 | Villeponteau et al. |
| 5,858,987 A | 1/1999 | Beer-Romero et al. |
| 5,879,713 A | 3/1999 | Roth et al. |
| 5,955,059 A | 9/1999 | Gilchrest et al. |
| 5,958,680 A | 9/1999 | Villeponteau et al. |
| 6,007,989 A | 12/1999 | West et al. |
| 6,015,710 A | 1/2000 | Shay et al. |
| 6,020,138 A | 2/2000 | Akhavan-Tafti |
| 6,046,307 A | 4/2000 | Shay et al. |
| 6,103,243 A | 8/2000 | Russell-Jones et al. |
| 6,130,088 A | 10/2000 | Monia et al. |
| 6,140,125 A | 10/2000 | Taylor et al. |
| 6,147,056 A | 11/2000 | Gilchrest et al. |
| 6,194,206 B1 | 2/2001 | West et al. |
| 6,320,039 B1 | 11/2001 | Villeponeau et al. |
| 6,440,650 B1 | 8/2002 | Matsuda et al. |
| 7,033,829 B2 | 4/2006 | Gilchrest et al. |
| 7,094,766 B1 | 8/2006 | Gilchrest et al. |
| 7,200,531 B2 | 4/2007 | Phillips et al. |
| 2003/0027167 A1 | 2/2003 | Hitoshi et al. |
| 2003/0032611 A1 | 2/2003 | Gilchrest et al. |
| 2003/0144233 A1 | 7/2003 | Phillips et al. |

FOREIGN PATENT DOCUMENTS

AU   717296   6/1996

(Continued)

OTHER PUBLICATIONS

Akiyama, M., et al., "Cytostatic Concentrations of Anticancer Agents do not Affect Telomerase Activity of Leukemic Cells in Vitro," European Jour. of Cancer, 35(2):309-315 (1999).

Anderson, W.F., "Human Gene Therapy," Nature, vol. 392, pp. 25-30 (Apr. 1998).

Anselmet, A., et al., "Non-Antisense Cellular Responses to Oligonucleotides," FEBS Letters, vol. 510, pp. 175-180 (2002).

Balasubramanian, S., et al., "Activation of telomerase and its association with G1-phase of the Cell Cycle During UVB-Induced Skin Tumorigenesis in SKH-1 Hairless Mouse," Oncogene, 18:1297-1302 (1999).

Balabhadrapathruni, S., et al., "Growth Inhibitory Effects of a Telomeric Oligonucleotide on MCF-7 Breast Cancer Cells," Abstract No. 3388 (Mar. 1997).

(Continued)

*Primary Examiner* — Amy Bowman
(74) *Attorney, Agent, or Firm* — Morgan, Lewis & Bockius LLP

(57) ABSTRACT

Described are methods for treating hyperproliferative disorders, including cancers, by administering to the affected mammal (e.g., human) an effective amount of a composition comprising one or more oligonucleotides which share at least 33% but less than 100% nucleotide sequence identity with the human telomere overhang repeat. Methods of treatment or prevention of hyperproliferative diseases or pre-cancerous conditions affecting epithelial cells, such as psoriasis, atopic dermatitis, or hyperprolferative diseases of other epithelia and methods for reducing photoaging, or oxidative stress or for prophylaxis against or reduction in the likelihood of the development of skin cancer, are also disclosed. The compositions and methods are also useful to treating other cancers.

2 Claims, 14 Drawing Sheets

FOREIGN PATENT DOCUMENTS

| | | |
|---|---|---|
| CA | 2224150 | 12/1996 |
| EP | 0 035 384 A2 | 9/1981 |
| GB | 2 336 157 A | 10/1999 |
| WO | WO 93/09788 | 5/1993 |
| WO | WO 93/12230 | 6/1993 |
| WO | WO 93/22431 | 11/1993 |
| WO | WO 94/08053 | 4/1994 |
| WO | WO 95/01773 | 1/1995 |
| WO | WO 95/07362 | 3/1995 |
| WO | WO 95/09175 | 4/1995 |
| WO | WO 96/23508 | 8/1996 |
| WO | WO 97/08314 | 8/1996 |
| WO | WO 96/27131 | 9/1996 |
| WO | WO 96/39152 | 12/1996 |
| WO | WO 96/40989 | 12/1996 |
| WO | WO 97/20924 | 6/1997 |
| WO | WO 97/38013 | 10/1997 |
| WO | WO 97/44450 | 11/1997 |
| WO | WO 98/06702 | 2/1998 |
| WO | WO 98/36066 | 8/1998 |
| WO | WO 99/03507 | 1/1999 |
| WO | WO 99/49042 | 9/1999 |
| WO | WO 01/18015 | 3/2001 |
| WO | WO 01/44465 | 6/2001 |
| WO | WO 01/74342 | 10/2001 |
| WO | WO 03/012125 | 2/2003 |

OTHER PUBLICATIONS

Beltz., L., et al., "The Effects of Telomerase Inhibitors on Lymphocyte Function,", Anticancer Research, 19:3205-3212 (1999).
Branch, A.D., "A Good antisense Molecule is Hard to Find," TIBS, vol. 23, pp. 45-50 (1998).
Chang, G.G., et al., "Inhibition of Human Cancer cell Growth by Periodate-oxidized 3-Aminopyridine Adenine Dinucleotide Diphosphate," International J. of Bio Chem., vol. 22, No. 11, pp. 1259-1269 (1990).
Chen, L., et al., "WRN, the Protein Deficient in Werner Syndrome, Plays a Critical Structural Role in Optimizing DNA Repair," Aging Cell, vol. 2, pp. 191-199 (2003).
Chen, Q., et al., "Oxidative DNA Damage and Senescence of Human Diploid Fibroblast Cells," Proc Natl Acad Sci USA vol. 92, pp. 4337-4341 (1995).
Cook, B., et al., "Role for the Related Poly(ADP-Ribose) Polymerases Tankyrase 1 and 2 at Human Telomeres," Molecular and Cellular Biology, vol. 22, No. 1, pp. 332-342 (2002).
Cruz, P.D., et al., "Thymidine Dinucleotides Inhibit Contact Hypersensitivity and Activate the Gene for tumor Necrosis Factor α," J. Investigative Dermatology, 114, pp. 253-258 (2000).
de Vries, T. J., et al., "Expression of gp100, MARTA-1, Tyrosinase and S100 in Paraffin-Embedded Primary Melanomas and Locoregional, Lymph Node, and Visceral Metastases: Implications for Diagnosis and Immunotherapy. A Study conducted by the EORTC Melanoma Cooperative Group," J. Pathology, vol. 193, pp. 13-20 (2001).
Ding, S., et al., "Genetic Variation in the Premature Aging Gene WRN: A Case-Control Study on Breast Cancer Susceptibility," Cancer Epidermal Biomarkers Prev., vol. 16, No. 2, pp. 263-269 (2007).
El-Deiry, W.S., et al., "WAF1, a Potential Mediator of p53 Tumor Suppression," Cell, 75:817-8-25 (1993).
Eller, M.S., et al., "The Effects of Oligonucleotide Size and 5001' Phosphate on Stimulation of Melanogenesis," J. Invest. Dermatol. Abstract No. 113, vol. 112, No. 4, p. 541 (1999).
Eller, M.S., et al., "Induction of Apoptosis by Telomere' 3' Overhang-Specific DNA," Experimental Cell Research, vol. 276, pp. 185-193 (2002).
Eller, M.S., et al., "Enhancement of DNA Repair in Human Skin Cells by Thymidine Dinucleotides: Evidence for a p53-Mediated Mammalian SOS Response," Proc. Natl. Acad. Sci, USA, vol. 94, pp. 12627-12632 (1997).
Eller, M.S., et al., "Induction of a p95/Nbs1-mediated S Phase Checkpoint by Telomere 3' Overhang Specific DNA," FASEB, vol. 17, pp. 152-162 (2003).
Eller, M.S., et al., "Activation of p53 Tumor Suppressor Protein by Thymidine Dinucleotides," Annual Meeting of the Society for Investigative Dermatology, Journal of Investigative Dermatology, vol. 106, No. 4, p. 835 (1996) XP002014518.
European Partial Search Report of European Patent Application No. 10002265.6 dated Jun. 14, 2010.
European Supplementary Search Report of European Application No. 03746759 dated May 25, 2009.
European Supplementary Search Report of European Application No. 03746759 dated Aug. 11, 2009.
European Supplementary Partial Search Report of European Application No. 04702134 dated Feb. 14, 2007.
European Supplementary Partial Search Report of European Application No. 04702134 dated May 29, 2007.
Fritsche, M., et al., "Induction of Nuclear Accumulation of the Tumor-Suppressor Protein p53 by DNA-damaging Agents," Oncogene 8:307-318 (1993).
Gerwirtz, et al., Blood, vol. 92, No. 3, pp. 712-736 (1998).
Glukhov, A. I., "Inhibition of Telomerase Activity of Melanoma Cells in Vitr by Antisense Oligonucleotides," Biochemical and Biophysical Research Communications, vol. 248, pp. 368-371 (1998).
Gomez-Navarro, et al., Gene Therapy for Cancer, European Journal of Cancer, vol. 35, pp. 867-885 (1999).
Goukassian, et al., DNA Oligonucleotide Treatment Corrects the Age-Associated Decline in DNA Repair Capacity, FASEB J., vol. 16, No. 7, pp. 754-756 (2002).
Goukassian, D.A. et al., "Topical DNA Oligonucleotide Therapy Reduces UV-induced Mutations and Photocarcinogenesis in Hairless Mice," Proc Natl Acad Sci USA, vol. 101, No. 11, pp. 3933-3938 (2004).
Granger, M., et al., "Telomerase in Cancer and Aging," Critical Review in Oncology Hematology, vol. 41, pp. 29-40 (2002).
Hadshiew, I.M., et al., "Stimulation of Malenogenesis by DNA Oligonucleotides: Effect of Size, Sequence and 5' Phosphorylation," Journal of Dermatological Science, pp. 127-138 (2001).
Harley, C.B., et al., "Telomerase, Checkpoints and Cancer," in Cancer Surveys—Advances and Prospects in Clinical, Epidemiological and Laboratory Oncology, Cold Spring Harbor Laboratory Press, 29:263-284 (1997).
Ho, P., et al., "Antisense Oligonucleotides as Therapeutics for Malignant Disease," vol. 24, No. 2, pp. 187-202 (Apr. 1997).
Hupp, T.R., et al., "Small Peptides Activate the Latent Sequence-Specific DNA Binding Function of p53,"Cell, 83, pp. 237-245 (1995).
International Search Report of PCT/US04/00819 dated Jul. 26, 2006.
International Searching Authority (ISA/US), "Written Opinion," Jul. 17, 2007, of PCT/US06/12468 filed Apr. 4, 2005.
Jayaraman, L., et al., "Activation of p53 Sequence-Specific DNA Binding by Short Single Strands of DNA Requires the p53 C-Terminus," Cell, 81:1021-1029 (1995).
Jen, et al., Stem Cells, vol. 18, pp. 307-319 (2000).
Kastan, M.B., et al., "A Mammalian Cell Cycle Checkpoint Pathway Utilizing p53 and GADD45 Is Defective in Ataxia-Telangiectasia," Cell, 71:587-597 (1992).
Kern, S.E., et al., "Oncogenic Forms of p53 Inhibit p53-Regulated Gene Expression," Science, 256:827-830 (1992).
Lee, M.S., "Telomeric DNA Induces p53-dependent reactive Oxygen Species and Protects Against Oxidative Damage," Journal of Dermatological Science, vol., No. 56, pp. 154-162 (2009).
Li, G.Z., et al., "Evidence that Exposure of the Telomere 3' Overhang Sequence Induces Senescence," Proc Natl Acad Sci USA, vol. 100, pp. 527-531 (2003).
Li, G.Z., et al., Signaling Pathway Requirements for Induction of Senescence by Telomere Homolog Oligonucleotides, Exp Cell Res, vol. 301, pp. 189-200 (2004).
Longe, H., et al., "Telomere Homolog Oligonucleotides Induce Apoptosis in Malignant But Not in Normal Lymphoid Cells: Mechanism and Therapeutic Potential," Int. J. Cancer, vol. 124, pp. 473-482 (2009).
Lu, et al., "Delivering siRNA in vivo for Functional Genomics and Novel Therapeutics," RNA Interference Technology, (Cambridge, Appasani ed.) pp. 303-317 (2005).
Lu, X., et al., "Differential Induction of Transcriptionally Active p53 Following UV or Ionizing Radiation: Defects in Chromosome Instability Syndromes?" Cell, 75:765-778 (1993).

Magnoni, C., et al., "Thymidine Dinucleotides Enhance DNA Repair in Normal Human Skin Cells," Annual Meeting of the Society for Investigative Dermatology, Journal of Investigative Dermatology 106 (4) (1996) XP002014517.

Maeda, T., et al., Enhanced Repair of Benzo(a)pyrene-induced DNA Damage in Human Cells Treated with Thymidine Dinucleotides, Mutation Res, vol. 433, pp. 137-145 (1999).

Mata, J., et a., "A Hexameric Phosporothioate Oligonucleotide Telomerase Inhibitor Arrests Growth of Burkitt's Lymphoma Cells in Vitro and in Viv," Toxicol. Appl. Pharmacol. 144:189-197 (1997).

Melnikova, V.O., et al., Mutation Research., vol. 571, pp. 91-106 (2005).

Mitchell, D.L. et al., "The Induction and Repair of DNA Photodamage in the Environment," In Environment UV Photobiology, A.R. Young, et al., eds. (Ny: Plenum Press), pp. 345-377 (1993).

Mitsudomi, T., et al., "p53 Gene Mutations in Non-Small-Cell Lung Cancer ell Lines and Their Correlation With the Presence of ras Mutations and Clinical Features," Oncogene 7:171-180 (1992).

Nelson, W.G., et al., "DNA Strand Breaks: The DNA Template Alterations That Trigger p53-Dependent DNA Damage Response Pathways," Mol. And Cell. Biol. 14(3):1815-1823 (1994).

Nicolaus, B.J.R., Symbiotic Approach to Drug Design, Decision Making in Drug Research, pp. 173-186 (1983).

Niggli, H.J., et al., "Sunlight-Induced Pyrimidine Dimers in Human Skin Fibroblasts in Comparison With Dimerization After Artificial UV-Irradiation," Photochemistry and Photobiology, 48(3):353-356 (1988).

Norton, J.E., et al., "Inhibition of Human Telomerase Activity by Peptide Nucleic Acids," Nature Biotechnology, vol. 14, pp. 615-619 (1996).

Ohnuma, T., et al., Inhibitory Effects of Telomere-Mimic Phosphorothioate Oligonucleotides on Various Hunan Tumor Cells in Vitro, Anticancer Research, No. 17, pp. 2455-2458 (1997).

Orkin, et al., Report and Recommendations of the Panel to Assess the NIH Investment in Research on Gene Therapy, Distributed by the National Institutes of Health, Dec. 7, 1995.

Page, D.T., et al., "Innovations in Oral Gene Delivery: Challenges and Potentials," vol. 6, No. 2, pp. 92-101 (Jan. 2001).

Page, T.J., et al., "The Cytotoxic Effects of Single-Stranded Telomere Mimics on OMA-BL1 Cells," Experimental Cell Research, vol. No. 252, pp. 41-49 (1999).

Parris, C.N., et al., "Telomerase Activity in Melanoma and Non-Melanoma Skin Cancer," British Jour. Of Cancer, 79(1):47-53 (1999).

Paull, T., et al., "A Mechanistic Basis for Mre11-Directed DNA Joining at Microhomologies," Proceedings of the National Academy of Sciences of the United States, vol. 97, No. 12, pp. 6409-6414 (2000).

Pedeux, R., et al., "Thymidine Dinucleotides Induce S Phase Cell Cycle Arrest in Additional to Increased Melanogenesis in Human Melanocytes," Journal of Investigative Dermatology, 111:472-477 (1998).

Petrini, J., et al., "Isolation and Characterization of the Human MRE11 Homologue," Genomics, vol. 29, No. 1, pp. 80-86 (1995).

Plenat, F., "Animal Models of Antisense Oligonucleotides: Lessons for Use in Humans," Molecular Medicine Today, pp. 250-257 (Jun. 1996)

Saeki, T., et al., "Inhibitory Effect of Telomere-Mimic Phosphorothioate Oligodeoxy Nucleotides (S-ODNS) in Human Tumor Cell Lines," Oncology, vol. 57, pp. 27-36 (1999).

Sanchez, Y., et al., "Regulation of RAD53 by the ATM-Like Kinases MEC1 and TEL1 in Yeast Cell Cycle Checkpoint Pathways," Science, 271:357-360 (1996).

Saretzki, G., et al., "Telomere Shortening Triggers a p53-Dependent Cell Cycle Arrest Via Accumulation of G-Rich Single Stranded DNA Fragments," Oncogene, vol. 18, pp. 5148-5158 (1999).

Stull, R.A., et al., "Antigene, Ribozyme and Aptamer Nucleic Acid Drugs: Progress and Prospects," vol. 12, No. 4, pp. 465-483 (1995).

Verma, I.M., et al., "Gene Therapy-Promises, Problems and Prospects," Nature, vol. 389, pp. 239-242 (Sep. 1997).

Voet, D., et al., "DNA Replication, Repair and Recombination," Biochemistry, Chap. 31, pp. 967-972 (1990).

Walworth, N. C. et al., "rad-Dependent Response of the chk1-Encoded Protein Kinase at the DNA Damage Checkpoint," Science, 271:353-356 (1996).

Wei, Q., et al., "DNA Repair and Aging in Basal Cell Carcinoma: A Molecular Epidemiology Study," Proc. Natl. Acad. Sci. USA 90:1614-1618 (1993).

White, et al., "Principles of Biochemistry," 6th Edition, pp. 182-183 (1978).

Wright, W.E., et al., "Experimental Elongation of Telomeres Extends the lifespan of immortal × normal cell hybrids," The EMBO Journal, 15(7):1734-1741 (1996).

Wu, K., et al., "Telomerase Activity and Telomere Length in Lymphocytes from patients with Cutaneous T-Cell Lymphoma," Cancer, 86(6):1056-1063 (1999)

Xu, M., et al., "Treatment of Cells With Mrell siRNA Increases Radiation Sensitivity and Reduces Heat Induced Radiosensitization," International Journal of Radiation Oncology Biology Physics, vol. 57, Supplement No. 2, pp. S144-145 (2003).

Yaar, M., et al., "Aging Versus Photoaging: Postulated Mechanisms and Effectors," The Society for Investigative Dermatology Symposium Proceedings, 3:47-51 (1998).

Yaar, M., et al., "The trk Family of Receptors Mediates Nerve Growth Factor and Neurotrophin-3 Effects in Melanocytes," J. Clin. Invest 94:1550-1562 (1994).

Zhihui, L., et al., "Inhibitory Effect of a Liposome-Mediated Antisense Oligodeoxynucleotide on Telomerase Activity in a Human Gastric Cancer Cell Line," Chinese Journal of Digestive Diseases, vol. 2, pp. 65-69 (2001).

Ziegler, M., et al., "A Cellular Survival Switch: Poly(ADP-ribosyl)ation Stimulates DNA Repair and Silences Transcription," BioEssays, vol. 23, pp. 543-548 (2001).

U.S. Appl. No. 08/467,012—Non-final office action dated Sep. 17, 1996.

U.S. Appl. No. 08/467,012—Non-final office action dated Jun. 10, 1997.

U.S. Appl. No. 08/467,012—Final office action dated Jan. 21, 1998.

U.S. Appl. No. 08/467,012—Notice of Allowance dated Mar. 16, 1999.

U.S. Appl. No. 09/048,927—Non-final office action dated Jun. 15, 1999.

U.S. Appl. No. 09/048,927—Final office action dated Jan. 12, 2000.

U.S. Appl. No. 09/048,927—Notice of Allowance dated Jun. 20, 2000.

U.S. Appl. No. 09/540,843—Restriction Requirement dated Jul. 3, 2001.

U.S. Appl. No. 09/540,843—Restriction Requirements dated Sep. 20, 2001.

U.S. Appl. No. 09/540,843—Non-final action dated Mar. 15, 2002.

U.S. Appl. No. 09/540,843—Non-final office action dated Nov. 18, 2002.

U.S. Appl. No. 09/540,843—Non-final office action dated Aug. 12, 2003.

U.S. Appl. No. 09/540,843—Final office action dated Feb. 26, 2004.

U.S. Appl. No. 09/540,843—Final office action dated May 10, 2005.

U.S. Appl. No. 09/540,843—Non-final office action dated Aug. 24, 2005.

U.S. Appl. No. 09/540,843—Notice of Allowance and Examiner's amendment dated Mar. 2, 2006.

U.S. Appl. No. 10/122,630—Restriction Requirement dated Nov. 21, 2003.

U.S. Appl. No. 10/122,630—Non-final office action dated Feb. 1, 2006.

U.S. Appl. No. 10/122,630—Final office action dated Oct. 19, 2006.

U.S. Appl. No. 10/122,630—Advisory action dated Mar. 19, 2007.

U.S. Appl. No. 10/122,633—Restriction Requirement dated Oct. 6, 2004.

U.S. Appl. No. 10/122,633—Non-final office action dated Feb. 23, 2005.

U.S. Appl. No. 10/122,633—Notice of Allowance dated Sep. 21, 2005.

U.S. Appl. No. 10/553,001—Restriction Requirement dated Apr. 2, 2009.

U.S. Appl. No. 10/553,001—Non-final office action dated Jun. 15, 2009.
U.S. Appl. No. 10/553,001—Final office action dated Mar. 25, 2010.
U.S. Appl. No. 10/553,001—Advisory Action dated Sep. 10, 2010.
U.S. Appl. No. 11/195,088—Restriction Requirement dated Mar. 17, 2006.
U.S. Appl. No. 11/195,088—Non-final action dated Jun. 13, 2006.
U.S. Appl. No. 11/195,088—Final office action dated Mar. 12, 2007.
U.S. Appl. No. 11/195,088—Non-final office action dated May 20, 2008.
U.S. Appl. No. 11/195,088—Final office action dated Jan. 29, 2009.
U.S. Appl. No. 11/195,088—Final Office Action dated Mar. 31, 2010.
U.S. Appl. No. 11/409,706—Non-final office action dated May 18, 2007.
U.S. Appl. No. 11/409,706—Final office action dated Feb. 7, 2008.
U.S. Appl. No. 11/409,706—Non-final office action dated Nov. 13, 2008.
U.S. Appl. No. 11/409,706 Non-final office action dated Jan. 27, 2010.
U.S. Appl. No. 12/275,089 Restriction Requirement dated Jul. 13, 2010.
U.S. Appl. No. 11/409,706 Non-final office action dated Oct. 14, 2010.
U.S. Appl. No. 12/709,378 Non-final office action dated Dec. 14, 2010.
U.S. Appl. No. 12/275,089 Non-final office action dated Oct. 12, 2010.

SEQUENCE LISTING

<160> NUMBER OF SEQ ID NOS: 40

<210> SEQ ID NO 1
<211> LENGTH: 9
<212> TYPE: DNA
<213> ORGANISM: Artificial Sequence
<220> FEATURE:
<223> OTHER INFORMATION: Synthetic DNA fragment

<400> SEQUENCE: 1 gagtatgag                                                              9

<210> SEQ ID NO 2
<211> LENGTH: 11
<212> TYPE: DNA
<213> ORGANISM: Artificial Sequence
<220> FEATURE:
<223> OTHER INFORMATION: Synthetic DNA fragment

<400> SEQUENCE: 2
gttagggtta g                                                          11

```
<210> SEQ ID NO 3
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 3
ctaaccctaa c                                                              11

<210> SEQ ID NO 4
<211> LENGTH: 11
<212> TYPE: DNA
<213> ORGANISM: Artificial Sequence
<220> FEATURE:
<223> OTHER INFORMATION: Synthetic DNA fragment

<400> SEQUENCE: 4
gtacgtacgt a                                                              11

<210> SEQ ID NO 5
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 5
gttagggtta g                                                              11

<210> SEQ ID NO 6
<211> LENGTH: 6
<212> TYPE: DNA
<213> ORGANISM: Artificial Sequence
<220> FEATURE:
<223> OTHER INFORMATION: Synthetic DNA fragment

<400> SEQUENCE: 6 ttaggg                                                                     6

<210> SEQ ID NO 7
<211> LENGTH: 6
<212> TYPE: DNA
<213> ORGANISM: Artificial Sequence
<220> FEATURE:
<223> OTHER INFORMATION: Synthetic DNA fragment

<400> SEQUENCE: 7 ttcggg                                                                     6

<210> SEQ ID NO 8
<211> LENGTH: 6
<212> TYPE: DNA
<213> ORGANISM: Artificial Sequence
<220> FEATURE:
<223> OTHER INFORMATION: Synthetic DNA fragment

<400> SEQUENCE: 8 ctaggg                                                                     6

<210> SEQ ID NO 9
<211> LENGTH: 6
<212> TYPE: DNA
<213> ORGANISM: Artificial Sequence
<220> FEATURE:
<223> OTHER INFORMATION: Synthetic DNA fragment

<400> SEQUENCE: 9
```

-continued

```
ttaggc                                                                  6

<210> SEQ ID NO 10
<211> LENGTH: 15
<212> TYPE: DNA
<213> ORGANISM: Artificial Sequence
<220> FEATURE:
<223> OTHER INFORMATION: Synthetic DNA fragment

<400> SEQUENCE: 10
ggtaggtgta ggatt                                                       15

<210> SEQ ID NO 11
<211> LENGTH: 15
<212> TYPE: DNA
<213> ORGANISM: Artificial Sequence
<220> FEATURE:
<223> OTHER INFORMATION: Synthetic DNA fragment

<400> SEQUENCE: 11
ggtaggtgta ggtta                                                       15

<210> SEQ ID NO 12
<211> LENGTH: 15
<212> TYPE: DNA
<213> ORGANISM: Artificial Sequence
<220> FEATURE:
<223> OTHER INFORMATION: Synthetic DNA fragment

<400> SEQUENCE: 12
ggttaggtgt aggtt                                                       15

<210> SEQ ID NO 13
<211> LENGTH: 16
<212> TYPE: DNA
<213> ORGANISM: Artificial Sequence
<220> FEATURE:
<223> OTHER INFORMATION: Synthetic DNA fragment

<400> SEQUENCE: 13
ggttaggtgg aggttt                                                      16

<210> SEQ ID NO 14
<211> LENGTH: 16
<212> TYPE: DNA
<213> ORGANISM: Artificial Sequence
<220> FEATURE:
<223> OTHER INFORMATION: Synthetic DNA Fragment

<400> SEQUENCE: 14
ggttaggtgt aggttt                                                      16

<210> SEQ ID NO 15
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 15
ggttaggtta ggtta                                                       15

<210> SEQ ID NO 16
<211> LENGTH: 15
<212> TYPE: DNA
<213> ORGANISM: Artificial Sequence
```

```
<220> FEATURE:
<223> OTHER INFORMATION: Synthetic DNA fragment

<400> SEQUENCE: 16
ggtaggtgta gggtg                                                          15

<210> SEQ ID NO 17
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 17 gttagggtt                                                                  9

<210> SEQ ID NO 18
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 18 ttagggtta                                                                  9

<210> SEQ ID NO 19
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 19
gttaggttta aggtt                                                          15

<210> SEQ ID NO 20
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 20
ggtcggtgtc gggtg                                                          15

<210> SEQ ID NO 21
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 21
ggcaggcgca gggcg                                                          15

<210> SEQ ID NO 22
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 22
gttagggtta gggtt                                                          15
```

```
<210> SEQ ID NO 23
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 23 gggttaggg                                                                    9

<210> SEQ ID NO 24
<211> LENGTH: 11
<212> TYPE: DNA
<213> ORGANISM: Artificial Sequence
<220> FEATURE:
<223> OTHER INFORMATION: Synthetic DNA Fragment
<220> FEATURE:
<221> NAME/KEY: misc_feature
<222> LOCATION: (1)..(11)
<223> OTHER INFORMATION: Nucleotides are connected via phosphorothioate
      linkage

<400> SEQUENCE: 24
gttagggtta g                                                                11

<210> SEQ ID NO 25
<211> LENGTH: 11
<212> TYPE: DNA
<213> ORGANISM: Artificial Sequence
<220> FEATURE:
<223> OTHER INFORMATION: Synthetic DNA Fragment
<220> FEATURE:
<221> NAME/KEY: misc_feature
<222> LOCATION: (1)..(2)
<223> OTHER INFORMATION: Nucleotides are connected via phosphorothioate
      linkage
<220> FEATURE:
<221> NAME/KEY: misc_feature
<222> LOCATION: (2)..(3)
<223> OTHER INFORMATION: Nucleotides are connected via phosphorothioate
      linkage
<220> FEATURE:
<221> NAME/KEY: misc_feature
<222> LOCATION: (9)..(10)
<223> OTHER INFORMATION: Nucleotides are connected via phosphorothioate
      linkage
<220> FEATURE:
<221> NAME/KEY: misc_feature
<222> LOCATION: (10)..(11)
<223> OTHER INFORMATION: Nucleotides are connected via phosphorothioate
      linkage

<400> SEQUENCE: 25
gttagggtta g                                                                11

<210> SEQ ID NO 26
<211> LENGTH: 11
<212> TYPE: DNA
<213> ORGANISM: Artificial Sequence
<220> FEATURE:
<223> OTHER INFORMATION: Synthetic DNA Fragment
<220> FEATURE:
<221> NAME/KEY: misc_feature
<222> LOCATION: (9)..(10)
<223> OTHER INFORMATION: Nucleotides are connected via phosphorothioate
      linkage
<220> FEATURE:
<221> NAME/KEY: misc_feature
<222> LOCATION: (10)..(11)
<223> OTHER INFORMATION: Nucleotides are connected via phosphorothioate
      linkage

<400> SEQUENCE: 26
```
gttagggtta g        11

<210> SEQ ID NO 27
<211> LENGTH: 11
<212> TYPE: DNA
<213> ORGANISM: Artificial Sequence
<220> FEATURE:
<223> OTHER INFORMATION: Synthetic DNA Fragment
<220> FEATURE:
<221> NAME/KEY: misc_feature
<222> LOCATION: (1)..(2)
<223> OTHER INFORMATION: Nucleotides are connected via phosphorothioate
      linkage
<220> FEATURE:
<221> NAME/KEY: misc_feature
<222> LOCATION: (2)..(3)
<223> OTHER INFORMATION: Nucleotides are connected via phosphorothioate
      linkage

<400> SEQUENCE: 27
gttagggtta g        11

<210> SEQ ID NO 28
<211> LENGTH: 17
<212> TYPE: DNA
<213> ORGANISM: Artificial Sequence
<220> FEATURE:
<223> OTHER INFORMATION: Synthetic DNA Fragment

<400> SEQUENCE: 28
ggttagggtg taggttt        17

<210> SEQ ID NO 29
<211> LENGTH: 16
<212> TYPE: DNA
<213> ORGANISM: Artificial Sequence
<220> FEATURE:
<223> OTHER INFORMATION: Synthetic DNA Fragment

<400> SEQUENCE: 29
ggttggttgg ttggtt        16

<210> SEQ ID NO 30
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 30
ggtggtggtg gtggt        15

<210> SEQ ID NO 31
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 31
ggaggaggag gagga        15

<210> SEQ ID NO 32
<211> LENGTH: 15
<212> TYPE: DNA
<213> ORGANISM: Artificial Sequence
<220> FEATURE:
<223> OTHER INFORMATION: Synthetic DNA Fragment

```
<400> SEQUENCE: 32
ggtgtggtgt ggtgt                                                    15

<210> SEQ ID NO 33
<211> LENGTH: 16
<212> TYPE: DNA
<213> ORGANISM: Artificial Sequence
<220> FEATURE:
<223> OTHER INFORMATION: Synthetic DNA Fragment

<400> SEQUENCE: 33 tgtggttgtgg tgtgg                                                   16

<210> SEQ ID NO 34
<211> LENGTH: 15
<212> TYPE: DNA
<213> ORGANISM: Artificial Sequence
<220> FEATURE:
<223> OTHER INFORMATION: Synthetic DNA Fragment

<400> SEQUENCE: 34
tagtgttagg tgtag                                                    15

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA Fragment

<400> SEQUENCE: 35
ggttggttgg ttggttggtt                                               20

<210> SEQ ID NO 36
<211> LENGTH: 16
<212> TYPE: DNA
<213> ORGANISM: Artificial Sequence
<220> FEATURE:
<223> OTHER INFORMATION: Synthetic DNA Fragment

<400> SEQUENCE: 36
ggttaggttt aggttt                                                   16

<210> SEQ ID NO 37
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 37 gagtatgag                                                            9

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA Fragment

<400> SEQUENCE: 38
gcatgcatgc attacgtacg                                               20

<210> SEQ ID NO 39
<211> LENGTH: 11
<212> TYPE: DNA
```

```
<213> ORGANISM: Artificial Sequence
<220> FEATURE:
<223> OTHER INFORMATION: Synthetic DNA Fragment

<400> SEQUENCE: 39
gatcgatcga t                                                           11

<210> SEQ ID NO 40
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 40 taggaggat                                                               9
```

METHOD TO INHIBIT CELL GROWTH USING OLIGONUCLEOTIDES

RELATED APPLICATIONS

This application is a continuation of U.S. application Ser. No. 11/195,088 filed Aug. 1, 2005, which is a continuation-in-part of U.S. application Ser. No. 10/122,630 filed Apr. 12, 2002, now abandoned, which is a continuation-in-part of International Application No. PCT/US01/10162 filed on Mar. 30, 2001, which is a continuation-in-part of U.S. application Ser. No. 09/540,843 filed Mar. 31, 2000, now U.S. Pat. No. 7,094,766, which is a continuation-in-part of U.S. application Ser. No. 08/952,697 filed Nov. 30, 1998, now abandoned, which is a continuation-in-part of U.S. application Ser. No. 09/048,927 filed Mar. 26, 1998, now U.S. Pat. No. 6,147,056, which is a continuation-in-part of International Application No. PCT/US96/08386 filed Jun. 3, 1996, which is a continuation-in-part of application Ser. No. 08/467,012 filed Jun. 6, 1995, now U.S. Pat. No. 5,955,059. The entire teachings of the above applications and issued patents are incorporated herein by reference.

BACKGROUND OF THE INVENTION

Mammalian cells have a complex response to DNA damage, as well as a tightly regulated program of replicative senescence, all suggested to be fundamental defenses against cancer [Campisi, J. (1996). *Cell* 84, 497-500]. In mammals, cell senescence is precipitated by critical shortening of telomeres, tandem repeats of the DNA sequence TTAGGG that cap the ends of chromosomes [Greider, C. W. (1996) *Annu Rev Biochem* 65, 337-365] and become shorter with each round of DNA replication. In germline cells and most cancer cells, immortality is associated with maintenance of telomere length by telomerase, an enzyme complex that adds TTAGGG repeats dues to the 3' terminus at the chromosome ends [Feng, J., et al. *Science* 269, 1236-1241; Harrington, L., et al., (1997) *Science* 275, 973-977; Nakamura, T. M., et al., (1997) *Science* 277, 955-957]. The catalytic subunit of telomerase is generally not expressed in normal somatic cells [Greider, C. W. (1996) *Annu Rev Biochem* 65, 337-365], and after multiple rounds of cell division critically shortened telomeres trigger either replicative senescence or death by apoptosis, largely dependent on cell type [de Lange, T. (1998) *Science* 279, 334-335], although the detailed mechanism is unknown. The mechanism by which telomeres participate in DNA damage responses has been less clear.

The frequency of cancer in humans has increased in the developed world as the population has aged. Melanoma and other skin cancers have increased greatly among aging populations with significant accumulated exposure to sunlight. For some types of cancers and stages of disease at diagnosis, morbidity and mortality rates have not improved significantly in recent years in spite of extensive research. Cancers are currently often treated with highly toxic therapies. Alternative therapies are needed that could take advantage of the natural mechanisms of the cells to repair environmental damage.

SUMMARY OF THE INVENTION

The present invention is directed to a composition comprising an oligonucleotide (T-oligo) having between 2 and 200 bases and having at least 33% but less than 100% identity with the sequence $(TTAGGG)_n$ where n=1 or greater and when said oligonucleotide comprises the sequence RRRGGG (R=any nucleotide) has a guanine content of 50% or less, said oligonucleotide optionally comprising an 5' phosphate.

Preferred embodiments of the present invention comprise one or more sequences selected from the group consisting of TT, TA, TG, AG, GG, AT, GT, TTA, TAG, TAT, ATG, AGT, AGG, GAG, GGG, GGT, TTAG, TAG, AGGG, GGTT, GTTA, TTAGGG, TAGGG, GGTTA, GTTAG, GGGTT, and GGGGTT.

In still another preferred embodiment of the present invention, the composition is between about 40% and 90% identical to $(TTAGGG)_n$. In another preferred embodiment, the compositions further comprise between about 2 and 20 oligonucleotides or between 50 and 11 nucleotides.

Among the most preferred embodiments of the present invention is an oligonucleotide having a sequence selected from the group consisting of:

| | |
|---|---|
| GGTTAGGGTGTAGGTTT; | (SEQ ID NO: 28) |
| GGTTGGTTGGTTGGTT; | (SEQ ID NO: 29) |
| GGTGGTGGTGGTGGT; | (SEQ ID NO: 30) |
| GGAGGAGGAGGAGGA; | (SEQ ID NO: 31) |
| GGTGTGGTGTGGTGT; | (SEQ ID NO: 32) |
| TAGTGTTAGGTGTAG; | (SEQ ID NO: 34) |
| GAGTATGAG; | (SEQ ID NO: 1) |
| AGTATGA; | |
| GTTAGGGTTAG; | (SEQ ID NO: 2) |
| GGTAGGTGTAGGATT; | (SEQ ID NO: 10) |
| GGTAGGTGTAGGTTA; | (SEQ ID NO: 11) |
| GGTTAGGTGTAGGTT; | (SEQ ID NO: 12) |
| GGTTAGGTGGAGGTTT; | (SEQ ID NO: 13) |
| GGTTAGGTTAGGTTA; | (SEQ ID NO: 15) |
| GGTTAGGTGTAGGTTT; | (SEQ ID NO: 14) |
| GTTAGGTTTAAGGTT; and | (SEQ ID NO: 19) |
| GTTAGGGTTAGGGTT. | (SEQ ID NO: 22) |

Another aspect of the invention encompasses the treatment of hyperproliferative disorders comprising administering to a human a composition comprising an oligonucleotide having between 2 and 200 bases, and having at least 33% but less than 100% identity with the sequence $(TTAGGG)_n$, where n=1 or greater, and when said oligonucleotide comprises the sequence RRRGGG (R=any nucleotide) has a guanine content of 50% or less, the oligonucleotide optionally comprising a 5' phosphate and optionally lacks cytosine.

Another aspect of the present invention is a method promoting differentiation of malignant cells in a mammal, the method comprising administering to the mammal an effective amount of a composition comprising an oligonucleotide therebetween 2 and 200 bases and having at least 33% but less than 100% identity with the sequence $(TTAGGG)_n$, and when said oligonucleotide comprises the sequence RRRGGG (R=any oligonucleotide) has a guanine content of 50% or less, said oligonucleotide optionally comprising a 5' phosphate and wherein said oligonucleotide optionally lacks cytosine.

The method is further directed to a method for inducing apoptosis in cancer cells in a human, the method comprising administering to the human an effective amount of a composition and comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide has a guanine content of 50% or less, and wherein said oligonucleotide optionally lacks cytosine.

Still another aspect of the present invention is a method for inhibiting the growth of cancer cells in a human, the method being independent of the presence or activity of telomerase in the cancer cells, the method comprising the step of administering to a human in an effective amount of a composition and comprising an oligonucleotide having between 2 and 200 bases and having at least 33% but less than 100% identity with the sequence (TTAGGG)$_n$, when said oligonucleotide comprises the sequence RRRGGG (R=any oligonucleotide has a guanine content of 50% or less.

A still further aspect of the invention is a method to inhibit the growth of cancer cells in a human. The method not requiring the presence or activity of p53 gene product in cancer cells, the method comprising administering a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

A still further aspect of the present invention is a method to inhibit the growth of cancer cells in a human, the method resulting in an S-phase arrest in said cells, the method comprising administering to the human an effective amount of a composition and comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

The invention is also directed to a method for preventing spongiosis, blistering, or dyskeratosis in the skin of a mammal following exposure to ultraviolet light, the method comprising apply to the skin an effective amount of a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

Also encompassed by the invention is a method for reducing the occurrences of skin cancer in a human, the method comprising applying to the skin an effective amount of a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

Another embodiment of the present invention is directed to methods to reduce the occurrence of skin cancer in a human with xeroderma pigmentosum or other genetically determined cancer predisposition, the method comprising applying to the skin, an effective amount of a composition comprising an oligonucleotide having between 2 and 200 bases and having at least 33% but less than 100% identity with the sequence (TTAGGG)$_n$, where n=1 or greater and cytosine and when said oligonucleotide comprises the sequence RRRGGG (R=any oligonucleotide) has a guanine content of 50% or less.

Also included in the present invention is a method for enhancing repair of ultraviolet irradiation induced damage to skin in a human in which the method includes applying to the skin an effective amount of a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

The invention is also directed to a method for reducing oxidative damage in a mammal. The method comprising administering to the mammal an effective amount of a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

The present invention is also directed to a method for reducing proliferation of keratinocytes in the skin of a human. The method complying applying to the skin a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

Still another embodiment comprises increasing DNA repair in cells and preferably in epithelial cells comprising contacting the epithelial cells with an effective amount of a composition comprising an oligonucleotide having between 2 and 200 bases and having at least 33% but less than 100% identity with the sequence (TTAGGG)$_n$, where n=1 or greater and when said oligonucleotide comprises the sequence RRRGGG (R=any oligonucleotide) has a guanine content of 50% or less.

Other oligonucleotides useful in the practice of any of the methods of the present invention are known as G-quadruplex DNAs, or alternatively G-tetraplex DNAs. Preferred G-quadruplex DNAs useful in the methods of the present invention comprise from about 3 nucleotides to about 200 nucleotides. Preferably the G-quadruplex DNA or RNA is at least 33% identical to (TTAGGG)$_n$ where n=1 or greater and preferably is less than 100% identical to (TTAGGG)$_n$, where n=1 or greater. More preferably, the G-quadruplex DNA is between 40% and 60% identical to (TTAGGG)$_n$. Preferably, the G-quadruplex DNA lacks cytosine. Preferably, when the G-quadruplex DNA comprises the sequence RRRGGG (R=any nucleotide), it has a guanine content of less than 50% and wherein said G-quadruplex DNA optionally comprises cytosine and preferably the G-quadruplex DNA has a 5' and/or 3' single strand.

A further method, useful in the treatment of cancers, is a method for enhancing the expression of one or more surface antigens indicative of differentiation of cancer cells in a human, the method comprising administering to the human an effective amount of an oligonucleotide of the present invention. The cells in this method can be, for example, melanoma, and the antigen can be, for example, MART-1, tyrosinase, TRP-1 or gp-100. The cells can, for example, be breast cancer cells and the antigen can be estrogen receptor α. Further, the invention is a method for inducing apoptosis in cancer cells in a human, said method comprising administering to the human an effective amount of a composition comprising one or more oligonucleotides which share at least 50% nucleotide sequence identity with the human telomere overhang repeat. This method can be applied, for example, to melanoma or to any other malignancy.

Thus, another method of the invention is a method for inducing senescence in cancer cells in a mammal (e.g., a human), the method comprising administering to the mammal an effective amount of a composition comprising one or more oligonucleotides encompassed by the present invention.

Also a part of the invention is a method for inhibiting the growth of cancer cells in a human, the method being independent of the presence or activity of telomerase in the cancer cells, in which the method includes the step of administering to the human an effective amount of a composition comprising one or more oligonucleotides encompassed by the present invention.

A further aspect of the invention is a method to inhibit the growth of cancer cells in a human, the method not requiring the presence or activity of p53 gene product in the cancer cells, the method comprising administering to the human an effective amount of a composition comprising one or more oligonucleotides as described above.

A further aspect of the invention is a method to inhibit the growth of cancer cells in a human, the method resulting in S-phase arrest in said cells, the method comprising administering to the human an effective amount of a composition comprising one or more oligonucleotides. The oligonucleotide to be used can be various lengths, but in one embodiment the oligonucleotide can be less than 6 nucleotides long.

The present invention is also directed to a method for preventing spongiosis, blistering or dyskeratosis in the skin of a mammal, following exposure to ultraviolet light, the method comprising applying to the skin an effective amount of a composition comprising one or more oligonucleotides.

Still another aspect of the invention is a method for reducing the occurrence of skin cancer in a human, the method comprising applying to the skin an effective amount of a composition comprising one or more oligonucleotides.

In another aspect of the methods of the present invention to reduce the occurrence of skin cancer in a human is a method for reducing the occurrence of skin cancer in a human with xeroderma pigmentosum, or other genetically determined cancer predisposition, the method comprising applying to the skin an effective amount of a composition comprising one or more oligonucleotides according to the present invention.

Also included in the invention is a method for enhancing repair of ultraviolet irradiation-induced damage to skin in a human, in which the method includes applying to the skin an effective amount of a composition comprising one or more oligonucleotides of the present invention.

Also included as an aspect of the invention is a method for reducing oxidative damage in a mammal, the method comprising administering to the mammal an effective amount of a composition comprising one or more oligonucleotides of the present invention.

It is also an object of the invention to provide a method for treating melanoma in a mammal, comprising administering to the mammal an effective amount of a composition comprising one or more oligonucleotides of the present invention. Various combinations of these oligonucleotides can also be used in the method.

It is also an object of the invention to provide a method for reducing proliferation of keratinocytes in the skin of a human, the method comprising applying to the skin an effective amount of a composition comprising one or more oligonucleotides according to the present invention. In particular applications of the method, the human to be treated has seborrheic keratosis, actinic keratosis, Bowen's disease, squamous cell carcinoma, or basal cell carcinoma. Another embodiment comprises increasing DNA repair in epithelial cells, comprising contacting said cells with an effective amount of a composition comprising at least one oligonucleotide, and a contiguous portion of any of the foregoing sequences. Preferred oligonucleotides for use in the methods of the present invention include but are not limited to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, and a fragment of any of the foregoing sequences, preferably including from about two nucleotides, more preferably 3 or more contiguous nucleotides of the full length oligonucleotide.

Also included in the invention are truncated versions of the above oligonucleotides identified above. The oligonucleotides of the present invention may be truncated by one or more nucleotides on the 5' end, the 3' end, or both the 5' end and the 3' end, so long as at least two contiguous nucleotides of the untruncated oligonucleotide remain. Preferably the truncated oligonucleotides have 10, 9, 8, 7, 6, 5, 4, 3 or 2 contiguous nucleotides found in the untruncated nucleotides.

Also a part of the invention are compositions comprising one or more oligonucleotides in a physiologically acceptable carrier, wherein the oligonucleotide comprises base sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:16, SEQ ID NO:17. Further, the invention can be a composition comprising one or more oligonucleotides in a physiologically acceptable carrier, wherein the oligonucleotide consists of base sequence SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

Preferred for applications in which it is desired to inhibit cell proliferation or to induce apoptosis are oligonucleotides comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:11, SEQ ID NO:12, SEQ ID NO:13, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

DETAILED DESCRIPTION OF THE INVENTION

Figure 1:
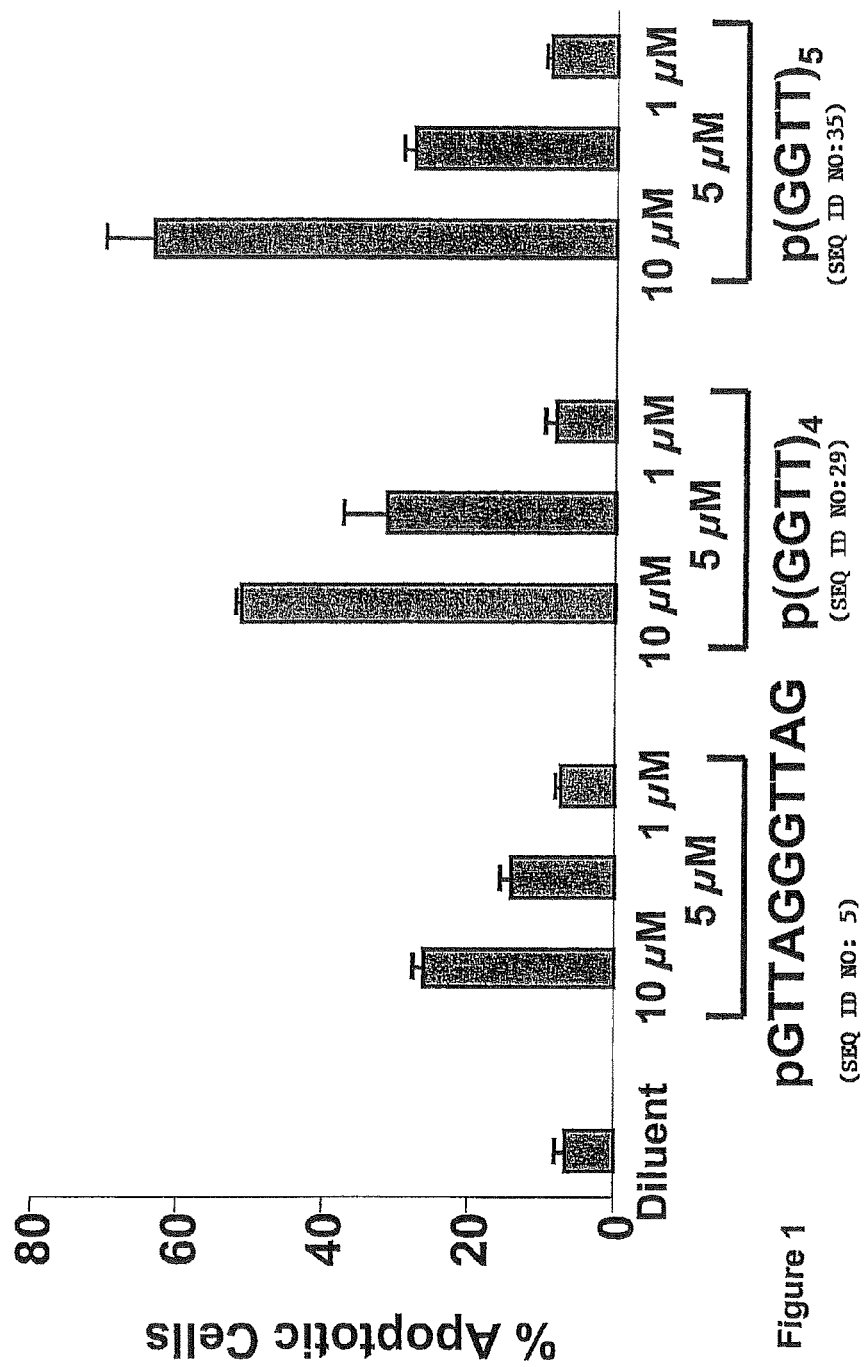
FIG. 1—Induction of apoptosis in MM-AN cells by a 16 mer and 20 mer oligonucleotide.

The present invention is based on the discovery that treatment of cells with oligonucleotides having at least 33% but less than 100% identity with the sequence $(TTAGGG)_n$ can elicit a variety of responses including inhibition of cell proliferation, apoptosis, induction of DNA repair a protective response to exposure to U.V.-irradiation, other ionizing radiation or carcinogenic chemicals and other results.

More specifically, the invention pertains to the use of such oligonucleotides a similar compounds, for the inhibition of cell proliferation the induction of senescence, or induction of apoptosis or induction of DNA repair. As used herein, inhibition of cell proliferation includes complete abrogation of cell division, partial inhibition of cell division and transient inhibition of cell division as measured by standard tests in the art and as described in the Examples herein and in PCT/US03/11393 which is incorporated herein by references. The invention also pertains to the prevention and/or treatment of hyperproliferative diseases, using the oligonucleotides of the present invention including, the diseases including but not limited to, cancer and pre-cancerous conditions, wherein the hyperproliferative disease affects cells of any organ and are of any embryonic origin. Tumors including metastatic tumors and cancers that have regrown or relapsed after treatment, as well as primary tumors, can be treated by the methods and materials of the invention. In particular embodiments, the diseases and conditions to be treated include skin diseases such as psoriasis and hyperproliferative, pre-cancerous or U.V.-induced dermatoses in mammals, particularly in humans as well as a variety of tumors including melanoma, breast cancer, prostate cancer, as well as a variety of cancer hematological malignancies, lung cancer, and other carcinomas.

The invention further pertains to use of the oligonucleotides of the present invention to reduce photoaging (a process due in part to cumulative DNA damage), and to reduce oxidative stress and oxidative damage. The invention also pertains to prophylaxis against, or reduction in the likelihood of, the development of skin cancer in a mammal using the oligonucleotides of the present invention. In addition, the compounds of the present invention can be used to induce apoptosis in cells such as cells that have sustained genetic mutation, such as malignant or cancer cells or cells from an actinic keratosis.

All types of cells, and in particular embodiments, epithelial cells, are expected to respond to the methods of the present invention as demonstrated by the representative in vitro and in vivo examples provided herein. Epithelial cells suitable for the method of the present invention include epidermal cells, respiratory epithelial cells, nasal epithelial cells, oral cavity cells, aural epithelial cells, ocular epithelial cells, genitourinary tract cells and esophageal cells, for example. Gastrointestinal cells are also contemplated in methods of the invention as described herein.

Cells that contain damaged or mutated DNA include, for exam*, actinic keratosis cells, cancer cells, cells that have been irradiated, as with U.V. light, and cells that have been exposed to DNA damaging chemicals or conditions will also respond to the oligonucleotides of the present invention. Inflammation, including allergically mediated inflammation involved in conditions such as atopic dermatitis, contact dermatitis, allergic rhinitis and allergic conjunctivitis may also be treated using the oligonucleotides of the present invention.

In one embodiment, the compositions of the present invention comprise DNA oligonucleotides approximately 2-200 bases in length, having at least 33% but less than 100% identity with the sequence $(TTAGGG)_n$ where n=1 or greater and optionally having a 5' phosphate and when said oligonucleotide comprises the sequence 5' RRRGGG-3' (R=any nucleotide) the oligonucleotide has a guanine content of 50% or less which can be administered to a mammal (e.g., human) in an appropriate vehicle. In another embodiment, the DNA oligonucleotides are about 2 to about 20 nucleotides in length. In still another embodiment, the oligonucleotides are about 5 to about 11 nucleotides in length. In yet another embodiment, the DNA oligonucleotides are about 2-5 nucleotides in length. Certain preferred embodiments of the oligonucleotides of the present invention lack cytosine. As used herein, "DNA oligonucleotide" refers to single-stranded DNA oligonucleotides, double-stranded DNA fragments, or a mixture of both single- and double-stranded DNA fragments.

It is understood that other base-containing sequences can also be used in the present invention, where bases are, for example, adenine, thymine, cytosine, or guanine. In one embodiment, the oligonucleotides of the present invention comprise a 5' phosphate. A combination of one or more of oligonucleotides of the present invention can also be used.

Other compositions useful in the practice of the present invention include G-quadruplex DNA, also known as DNA tetraplexes. Guanine bases in solution can form a structure consisting of four bases in a planar array and held together by Hoogsteen hydrogen bonds, called G-quadruplexes or tetraplexes. Similarly, poly(G) homopolymers also form 4-stranded nucleic acid structures with stacked guanine tetrads. In DNA, guanine tetraplexes can form from intrastrand or interstrand associations with 2 or more of the tetrads stacked upon each other to stabilize the complex. These strands can run in a parallel or an anti-parallel fashion with non G-rich DNA looped out and connecting the tetrad cores.

For many years, G-quadruplexes were considered to be an interesting but non-biologically relevant phenomenon. However, recently G-quadruplexes have been suggested to be important in immunoglobulin heavy chain recombination and in the regulation of the retinoblastoma and c-myc genes. Also, G-quadruplexes have been shown to form in single-stranded telomeric DNA, particularly in the 3' overhang. Although the function of these G-quadruplexes in telomeres, if any, is unclear, it has been postulated that they may play a role in protein recognition and telomere recombination. More recently, G-quadruplex formation in telomeric DNA was shown to inhibit telomere elongation by telomerase and ligands that stabilize G-quadruplexes are now in trials as telomerase inhibitors and anticancer agents.

Theoretically, G-quadruplexes could stall the procession of DNA and RNA polymerases, hindering DNA replication and translation, situations that could lead to increased DNA recombination and mutation. Two DNA helicases have been identified that have a high affinity for these unusual DNA structures and can resolve them efficiently; Wrn and Blm, the helicases mutated in the diseases Werner Syndrome and Bloom Syndrome, respectively. Wrn is of particular interest because it contains both 3' to 5' helicase and exonuclease activities and is able to catalyze the structure-dependent degradation of DNA containing aberrant structures such as bubbles, loops and hairpins and of G-rich telomeric DNA specifically. Furthermore, cells from Werner Syndrome patients shows signs of impaired telomere maintenance such as accelerated telomere shortening and defective lagging strand synthesis (20). Because of Wrn's preference for unusual DNA structures, it is possible that Wrn-mediated telomere functions depend, at least in part, on the ability of single-stranded telomeric DNA, particularly the 3' overhang, to form G-quadruplex structures.

We have shown that small DNA oligonucleotides homologous to the telomere 3' overhang (T-oligos) induce DNA damage responses in normal and transformed mammalian cells and that these responses are largely dependent on Wrn and the degradation of these oligonucleotides. The best studied of these oligonucleotides to date is the 11mer GTTAGGGTTAG (SEQ ID NO:5). It is possible that Wrn-mediated degradation of these oligonucleotides initiates these DNA damage responses. However, we have found that oligonucleotides other than those 100% identical to the telomere repeat sequence of (TTAGGG)$_n$ are also very potent inducers of these DNA damage responses as described herein. For example, the 16-mer GGTTGGTTGGTTGGTT (SEQ ID NO:29) and the 20-mer GGTTGGTTGGTTGGTTGGTT (SEQ ID NO:35) are the most potent inducers of the DNA damage response found to date. Because of the ability of these T-oligos to form an intrastrand G-quartet stabilized by 2 overlapping planar G-tetrads (the interstrand G-quartet formed by GTTAGGGTTAG (SEQ ID NO:5) would be less stable), we believe that the activity of T-oligos depends at least in part on their ability to form these stable, intrastrand G-quartets. These structures would be excellent substrates for the Wrn helicases/exonuclease and, accordingly, are likely to be the most active inducers of the DNA damage responses.

PCT/US03/11393

PCT/US03/11393 from which the present application claims priority describes the use of a nine-nucleotide oligomer, GAGTATGAG (SEQ ID NO:1) that stimulates melanogenesis in human melanocytes and induced the expression of p21/Waf/Cip 1, a growth inhibitory gene product in a squamous cell carcinoma cell line. Furthermore, TAGGAGGAT (SEQ ID NO:40) (5/9 identity with telomere overhang repeat), and truncated versions of the original 9mer, AGTATGA and GTATG, also stimulated melanogenesis in human melanocytes. In addition, the sequence pGTTAGGGTTAG (SEQ ID NO:5) stimulated pigmentation in Cloudman S91 melanoma cells and induced apoptosis in a human T-cell line. The oligonucleotide pGTTAGGGTTAG (SEQ ID NO:5) induced human T cells to undergo apoptosis, while CTAACCCTAAC (SEQ ID NO:3) and pGATCGATCGAT (SEQ ID NO:39) did not significantly increase apoptosis in these cells.

The compounds of the present invention are therefore useful in methods of inhibiting cell proliferation, preventing cancer, photoaging and oxidative stress by enhancing DNA repair, and, in the skin, by enhancing pigmentation through increased melanin production. Melanin is known to absorb photons in the U.V. range and therefore its presence reduces the risk of cancer and photoaging.

The DNA fragments, oligonucleotides, deoxynucleotides, dinucleotides, and dinucleotide dimers can be obtained from any appropriate source, or can be synthetically produced. To make DNA fragments, for example, salmon sperm DNA can be dissolved in water, and then the mixture can be autoclaved to fragment the DNA. In one embodiment, the DNA fragments, oligonucleotides, deoxynucleotides, dinucleotides or dinucleotide dimers comprise a 5' phosphate.

The compounds of the present invention also play a protective role in U.V.A-induced oxidative damage to the cell (see e.g. Example 15 of PCT/US03/11393). Thus, in one embodiment of the present invention, the compounds of the present invention are administered to cells to protect against oxidative damage. In one embodiment, these compounds are topically administered to the epidermis of an individual.

An "agent that increases activity of p53 protein," as used herein, is an agent (e.g., a drug, molecule, nucleic acid fragment, oligonucleotide, or nucleotide) that increases the activity of p53 protein and therefore results in increase in an DNA repair mechanisms, such as nucleotide excision repair, by the induction of proteins involved in DNA repair, such as PCNA, XPB and p21 proteins. The activity of p53 protein can be increased by directly stimulating transcription of p53-encoding DNA or translation of p53-specific mRNA, by increasing expression or production of p53 protein, by increasing the stability of p53 protein, by increasing the resistance of p53 mRNA or protein to degradation, by causing p53 to accumulate in the nucleus of a cell, by increasing the amount of p53 present, by phosphorylating the serine 15 residue in p53, or by otherwise enhancing the activity of p53. A combination of more than one agent that increases the activity of p53 can be used. Alternatively or in addition, the agent that increases the activity of p53 can be used in combination with DNA fragments, deoxynucleotides, or dinucleotides, as described above.

Ultraviolet irradiation produces DNA photoproducts that when not promptly removed, can cause mutations and skin cancer. Repair of U.V.-induced DNA damage requires efficient removal of the photoproducts to avoid errors during DNA replication. Age-associated decrease in DNA repair capacity is associated with decreased constitutive levels of p53 and other nuclear excision repair (NER) proteins required for removing U.V.-induced photoproducts. Compounds of the present invention induced NER proteins in human dermal cells when these cells were treated with these compounds before U.V. irradiation (see Example 16 of PCT/US03/11393). While there were age related decreases in NER proteins, NER proteins in cells from donors of all ages from newborn to 90 years were induced by 200-400%. A significant decrease in the rate of repair of thymine dimers and photoproducts occurs with increased age of the cell sample; however, cells that were pre-treated with compounds of the present invention, then U.V. irradiated, removed photoproducts 30 to 60 percent more efficiently. Thus, the treatment of cells with small DNA oligonucleotides partially compensates for age-associated decreases in DNA repair capacity. In light of the in vivo efficacy of the compounds of the present invention, it is reasonable to expect that treatment of human skin with the compounds of the present invention enhances endogenous DNA repair capacity and reduces the carcinogenic risk from solar U.V. irradiation. This method is especially useful in older individuals who likely have reduced cellular DNA repair capacity.

DNA fragments, oligonucleotides, deoxynucleotides, dinucleotides or dinucleotide dimers, to be applied to the skin in methods to prevent the sequelae of U.V. exposure or to reduce the occurrence of skin cancer, to reduce oxidative damage, or to enhance repair of U.V.-induced damage, can be administered alone, or in combination with physiologically acceptable carriers, including solvents, perfumes or colorants, stabilizers, sunscreens or other ingredients, for medical or cosmetic use. They can be administered in a vehicle, such as water, saline, or in another appropriate delivery vehicle. The delivery vehicle can be any appropriate vehicle which delivers the DNA fragments, oligonucleotides, deoxynucleotides, dinucleotides, or dinucleotide dimers. In one embodiment, the concentration of oligonucleotide can be 10 µM-100 µM.

To allow access of the active ingredients of the composition to deeperlying skin cells, vehicles which improve penetration through outer layers of the skin, e.g., the stratum corneum, are useful. Vehicle constituents for this purpose include, but are not limited to, ethanol, isopropanol, diethylene glycol ethers such as diethylene glycol monoethyl ether, azone (1-dodecylazacycloheptan-2-one), oleic acid, linoleic acid, propylene glycol, hypertonic concentrations of glycerol, lactic acid, glycolic acid, citric acid, and malic acid. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used.

In another embodiment, a liposome preparation can be used. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al., all of which are incorporated herein by reference can be used. The compositions of the invention intended to target skin conditions can be administered before, during, or after exposure of the skin of the mammal to U.V. or agents causing oxidative damage. Other suitable formulations can employ niosomes. Niosomes are lipid vesicles similar to liposomes, with membranes consisting largely of non-ionic lipids, some forms of which are effective for transporting compounds across the stratum corneum.

Other suitable delivery methods intended primarily for skin include use of a hydrogel formulation, comprising an aqueous or aqueous-alcoholic medium and a gelling agent in addition to the oligonucleotide(s). Suitable gelling agents include methylcellulose, carboxymethylcellulose, hydroxypropylmethylcellulose, carbomer (carbopol), hypan, polyacrylate, and glycerol polyacrylate.

In one embodiment, oligonucleotides, or composition comprising one or more of the foregoing, is applied topically to the skin surface. In other embodiments, the DNA fragments, oligonucleotides, deoxynucleotides, dinucleotides, dinucleotide dimers, or composition comprising one or more of the foregoing, is delivered to other cells or tissues of the body such as epithelial cells. Cells of tissue that is recognized to have a lesser barrier to entry of such substances than does the skin can be treated, e.g., orally to the oral cavity; by aerosol to the respiratory epithelium; by instillation to the bladder epithelium; by instillation or suppository to intestinal (epithelium) or by other topical or surface application means to other cells or tissues in the body, including eye drops, nose drops and application using angioplasty, for example. Furthermore, the oligonucleotides of the present invention can be administered intravenously or injected directly into the tissue of interest intracutaneously, subcutaneously, intramuscularly or intraperitoneally, along with a pharmaceutically acceptable carrier. In addition, for the treatment of blood cells, the compounds of the present invention can be administered intravenously or during extracorporeal circulation of the cells, such as through a photophoresis device, for example. As demonstrated herein, all that is needed is contacting the cells of interest with the oligonucleotide compositions of the present invention, wherein the oligonucleotides contacting the cells can be as small as dinucleotides.

The oligonucleotides, deoxynucleotides, dinucleotides, dinucleotide dimers, agent that promotes differentiation, agent that increases p53 activity, or composition comprising one or more of the foregoing, is administered to (introduced into or contacted with) the cells of interest in an appropriate manner. The "cells of interest," as used herein, are any cells which may become affected or are affected by the hyperproliferative disease precancerous condition or cancerous conditions, or cells which are affected by oxidative stress, DNA damaging conditions such as U.V. irradiation or exposure to damaging DNA chemicals such as benzo[a]pyrene. Preferred cells are epithelial cells, including melanocytes and keratinocytes, as well as other epithelial cells such as oral, respiratory, bladder and cervical epithelial cells. As demonstrated herein, methods and compositions of the present invention can inhibit growth, induce melanogenesis and induce TNFa production in epithelial cells from numerous sources.

The oligonucleotides, DNA fragments, deoxynucleotides, dinucleotides, dinucleotide dimers, agent that promotes differentiation, that increases p53 activity, or compositions comprising one or more of the foregoing, is applied at an appropriate time, in an effective amount. The "appropriate time" will vary, depending on the type and molecular weight of the oligonucleotides, DNA fragments, deoxynucleotides, dinucleotides, dinucleotide dimers, or other agent employed, the condition to be treated or prevented, the results sought, and the individual patient. An "effective amount," as used herein, is a quantity or concentration sufficient to achieve a measurable desired result. The effective amount will depend on the type and molecular weight of the oligonucleotides, DNA fragments, deoxynucleotides, dinucleotides, dinucleotide dimers, or agent employed, the condition to be treated or prevented, the results sought, and the individual patient. For example, for the treatment or prevention of psoriasis, or for hyperproliferative, cancerous, or pre-cancerous conditions, or U.V.-induced dermatoses, the effective amount is the amount necessary to reduce or relieve any one of the symptoms of the disease, to reduce the volume, area or number of cells affected by the disease, to prevent the formation of affected areas, or to reduce the rate of growth of the cells affected by a hyperproliferative disorder. The concentration can be approximately 2-300 µM. In a another embodiment, the concentration of agent (e.g., oligonucleotide) is about 50-200 µM; in another embodiment, the concentration is about 75-150 µM. For some applications, the concentration of oligonucleotide can be about 10-100 µM.

In one embodiment of the present invention, oligonucleotides, agent that increases p53 activity, that promotes differentiation, or a composition that can comprise one or more of the foregoing, is administered, in an appropriate delivery vehicle, to the cells of interest in the mammal in order to treat or prevent a hyperproliferative disease affecting epithelial cells. The oligonucleotides, that promote differentiation, agent that increases p53 activity, or composition comprising one or more of the foregoing, can be administered systemically, can be administered directly to affected areas, or can be applied prophylactically to regions commonly affected by the hyperproliferative disease.

In another embodiment, the DNA fragments, oligonucleotides, deoxynucleotides, dinucleotides, dinucleotide dimers, agent that increases p53 activity, agent that promotes differentiation, or composition comprising one or more of the foregoing, is administered to the epidermis for the treatment or prevention of oxidative stress or for the treatment or prevention of hyperproliferative, cancerous, or pre-cancerous conditions, or LJV-responsive dermatoses.

In still another embodiment, DNA fragments, oligonucleotides, deoxynucleotides, dinucleotides, dinucleotide dimers, agent that promotes differentiation, agent that increases p53 activity, or a composition comprising one or more of the foregoing, can be administered, either alone or in an appropriate delivery vehicle, to the epidermis for reduction of photoaging, or prophylaxis against or reduction in the likelihood of development of skin cancer. The DNA fragments, oligonucleotides, deoxynucleotides, dinucleotides, dinucleotide dimers, agent that promotes differentiation, agent that increases p53 activity, or composition comprising one or more of the foregoing, can be administered topically or by intracutaneous injection at an appropriate time (i.e., prior to exposure of the skin to U.V. irradiation). The DNA fragments, oligonucleotides, deoxynucleotides, dinucleotides, dinucleotide dimers, agent that promotes differentiation, agent that increases p53 activity, or composition comprising one or more of the foregoing, can be applied before, during or after exposure to a carcinogen such as U.V. irradiation. They can be applied daily or at regular or intermittent intervals. In one embodiment, the DNA fragments, oligonucleotides, deoxynucleotides, dinucleotides, dinucleotide dimers, agent that promotes differentiation, agent that increases p53 activity, or composition comprising one or more of the foregoing, can be administered on a daily basis to skin which may be exposed to sunlight during the course of the day.

In a further embodiment of the invention, the DNA fragments, oligonucleotides, deoxynucleotides, dinucleotides, dinucleotide dimers, agent that promotes differentiation, agent that increases p53 activity, or composition comprising one or more of the foregoing, is administered, in an appropriate delivery vehicle, to an individual (e.g., epithelial cells or other cells of an individual) for the treatment or prevention of hyperproliferative, cancerous or pre-cancerous conditions, or to repair or prevent DNA damage caused by DNA damaging chemicals, such as benzo[a]pyrene.

As demonstrated herein, the compounds of the present invention are active in vitro and in vivo in their unmodified form, e.g., sequences of unmodified oligonucleotides linked by phosphodiester bonds. As used herein, the terms "oligonucleotide," "dinucleotide," "DNA fragment," etc., refer to molecules having deoxyribose as the sugar, and having phosphodiester linkages ("phosphate backbone") as occur naturally, unless a different linkage or backbone is specified.

Furthermore, although not necessary for the ability to elicit the U.V. mimetic effects of the present invention, the compounds of the present invention can be modified, derivative or otherwise combined with other reagents to increase the half life of the compound in the organism and/or increase the uptake of these compounds by the cells of interest. Modification reagents include, for example, lipids or cationic lipids.

In one embodiment, the compounds of the present invention are covalently modified with a lipophilic group, an adamancy moiety. The compounds of the present invention can be modified to target specific tissues in the body. For example, brain tissue can be targeted by conjugating the compounds with biotin and using the conjugated compounds with an agent that facilitates delivery across the blood-brain barrier, such as antitransferring receptor antibody coupled to streptavidin.

PCT/US03/11393 demonstrates that telomere homolog oligonucleotides but not complementary or unrelated DNA sequences of the same length induce an S-phase arrest and apoptosis in an established human lymphocyte line and in a human melanoma cell line.

Experimental telomere disruption [Karlseder, J., et al., 1999, Science 283: 1321-1325] and cellular manipulations that precipitate premature senescence, such as transfection with the ras oncogene or exposure to oxidative stress, are known to digest the 3' telomere overhang and/or to shorten overall telomere length. In contrast, exposure of cells to telomere homolog oligonucleotides in the present studies increases mean telomere length (MTL). While not wishing to be bound by a single mechanism, these data strongly suggest that the oligonucleotides can activate telomerase, presumably by inducing TERT, and imply that transient activation of telomerase may be a part of the physiologic telomere-based DNA damage response that also includes activation of the ATM kinase with subsequent signaling through p53 and p95/Nbs 1. The apparent ability of oligonucleotides to induce this response in the absence of DNA damage and telomere disruption offers the possibility of "rejU.V.enating" cells through telomere elongation, as recently reported in human skin equivalent constructs containing fibroblasts transfected with TERT, without the enhanced risk of carcinogenesis observed even in even normal cells that ectopically express telomerase. Equally, the phenomenon suggests that the advantages of robust DNA damage responses of the type observed in p53 overexpressing mice could be separated from the premature senescence also observed in the transgenic animals (Tyner, S. D., et al., 2002, Nature 415: 45-523). Such "rejuvenation" or delay in acquiring the senescent phenotype associated with critical telomere shortening would be in addition to other benefits that might accrue from treatment with oligonucleotides partially or completely homologous to the $(TTAGGG)_n$ repeated sequence. Based on extensive work in vivo as well as in vitro, these are understood to include sunless tanning and related photoprotection, enhanced DNA repair capacity, cancer prevention and treatment, and immunomodulation.

Under normal conditions, the 3' telomere overhang DNA sequence is believed to be folded back and concealed in a loop structure stabilized by TRF2 [Griffith, J. D., et al., (1999), Cell 97, 503-514]. However, this sequence might be exposed if the telomere were distorted, for example by ultraviolet (U.V.)-induced thymine dimers or carcinogen adducts involving guanine residues (as with cisplatin or benzo[a]pyrene) that could render the loop-back configuration unstable. Exposure of the TTAGGG (SEQ ID NO:11) repeat sequence could be the initial signal leading to a variety of DNA damage responses, dependent on cell type as well as intensity and/or duration of the signal. These responses include cell cycle arrest, apoptosis, and a more differentiated sometimes adaptive phenotype, for example, increased melanin production (tanning).

The proposed model predicts that inability to repair damage to telomeric DNA would lead to exaggerated damage responses, such as p53 induction and apoptosis, as has been reported for LJV-irradiated xeroderma pigmentosum cells that cannot efficiently remove DNA photoproducts (Dumaz, N., et al., 1998, *Carcinogenesis* 19: 1701-1704). This model is further consistent with the recent finding that transgenic mice with supra-normal p53 activity are highly resistant to tumors, yet age prematurely (Tyner, S. D., et al., 2002, *Nature* 415: 45-523). A DNA damage recognition mechanism might have evolved to contain predominantly thymidine and guanine bases. The TTAGGG$_n$ repeat sequence is an excellent target for DNA damage, as dithymidine sites most commonly participate in formation of U.V. photoproducts (Setlow, R. B. and W. L. Carrier. 1966, *J Mol Biol* 17: 237-254) and guanine is both the principal site of oxidative damage, forming 8-oxoguanine [Kasai, H. and S. Nishimura, 1991. "Oxidative Stress: Oxidants and Antioxidants," pp. 99-116 In H. Sies (ed.) (London, Academic Press, Ltd.)], as well as the base to which most carcinogens form adducts [Fnedberg, E. C., et al., 1995, pp. 1-58 In E. C. Friedberg, G. C. Walker and W. Siede, eds.

The invention includes methods for treating a hyperproliferative disorder in a mammal, in which the therapy includes administering to the mammal an effective amount of a composition comprising one or more oligonucleotides as described herein. These methods can be applied especially to human subjects. Hyperproliferative disorders can be characterized by benign growth of cells beyond a normal range, and which sometimes may result in a benign tumor or widespread epidermal thickening, as in psoriasis. Also among the various hyperproliferative disorders to be treated by these methods are cancer as it is manifested in various forms and arising in various cell types and organs of the body, for example, cervical cancer, lymphoma, osteosarcoma, melanoma and other cancers arising in the skin, and leukemia. Also among the types of cancer cells to which the therapies are directed include but are not limited to breast, lung, liver, prostate, pancreatic, ovarian, bladder, uterine, colon, brain, esophagus, stomach, and thyroid.

The oligonucleotides can be administered in the methods of treatment described herein as a single type of oligonucleotide or in a combination comprising with one or more different oligonucleotides. Oligonucleotides without a 5' phosphate can be used in any of the methods of therapy for treatment, or for the reduction of incidence of a disease or disorder described herein. However, oligonucleotides having a 5' phosphate are preferred, as it has been shown that the 5' phosphate improves uptake of the oligonucleotide into cells. The oligonucleotides can be at least 2 nucleotides in length, preferably 2-200 nucleotides, and more preferably from 2 to 20 nucleotides in length. Oligonucleotides 5-11 nucleotides are more preferred.

Other methods of treatment for hyperproliferative diseases including cancer that are encompassed by the present invention include the administration of one or more oligonucleotides of the present invention in combination with one or more chemotherapeutic agents. Such chemotherapeutic agents include, but are not limited to vincristine, doxorubicin, prednisone, cyclophosphamide, busulphan, cisplatin, methotrexate, melphelan, chlorambucal, ra-c bleomycin, etoposide, fluorouroul and mitomycin as well as anticancer monoclonal antibodies such as Rituxin.

Oligonucleotides are relatively short polynucleotides. Polynucleotides are linear polymers of nucleotide monomers in which the nucleotides are linked by phosphodiester bonds between the 3' position of one nucleotide and the 5' position of the adjacent nucleotide. Unless otherwise indicated, the "oligonucleotides" of the invention as described herein have a phosphodiester backbone.

To enhance delivery through the skin, the oligonucleotides of the invention may be modified so as to either mask or reduce their negative charges or otherwise alter their chemical characteristics. This may be accomplished, for example, by preparing ammonium salts of the oligonucleotides using readily available reagents and methods well known in the art. Preferred ammonium salts of the oligonucleotides include trimethyl-, triethyl-, tributyl-, tetramethyl-, tetraethyl-, and tetrabutyl-ammonium salts. Ammonium and other positively charged groups can be covalently bonded to the oligonucleotide to facilitate its transport across the stratum corneum, using an enzymatically degradable linkage that releases the oligonucleotide upon arrival inside the cells of the viable layers of the epidermis.

Another method for reducing or masking the negative charge of the oligonucleotides includes adding a polyoxyethylene spacer to the 5' phosphate groups of the oligonucleotides and/or the internal phosphates of the oligonucleotides using methods and reagents well known in the art. This, in effect, adds a 6- or 12-carbon modifier (linker) to the phosphate that reduces the net negative charge by +1 and makes the oligonucleotides less hydrophilic. Further negative charge reduction is achieved by adding a phosphoroamidite to the end of the polyoxyethylene linker, thereby providing an additional neutralizing positive charge.

The phosphodiester backbone of the oligonucleotides of the present invention can also be modified or synthesized to reduce the negative charge. A preferred method involves the use of methyl phosphonic acids (or chiral methylphosphonates), whereby one of the negatively charged oxygen atoms in the phosphate is replaced with a methyl group. These oligonucleotides are similar to oligonucleotides having phosphorothioate linkages which comprise a sulfate instead of a methyl group and which are also within the scope of the present invention.

The oligonucleotides of the present invention can also take the form of peptide nucleic acids (PNAs) in which the bases of the nucleotides are connected to each other via a peptide backbone.

Other modifications of the oligonucleotides such as those described, for example, in U.S. Pat. Nos. 6,537,973 and 6,506,735 (both of which are incorporated herein by reference for all of the oligonucleotide modifications described therein) and others will be readily apparent to those skilled in the art.

The oligonucleotides can also be "chimeric" oligonucleotides which are synthesized to have a combination of two or more chemically distinct backbone linkages, one being phosphodiester. In one embodiment are chimeric oligonucleotides with one or more phosphodiester linkages at the 3' end. In another embodiment are chimeric oligonucleotides with one or more phosphodiester linkages at the 3' and 5' ends.

As reported in Example 46 of PCT/US03/11393, 11-mer oligonucleotides with sequence SEQ ID NO:5 were synthesized to contain phosphodiester linkages throughout, phosphorothioate linkages throughout, or a combination of linkages. One oligonucleotide had two phosphorothioate linkages at the 5' end; another oligonucleotide had two phosphorothioate linkages at the 3' end; still another had two phosphorothioate linkages at each end. Oligonucleotides with phosphodiester linkages at the 3' end were found to be the most effective at stimulating reactions associated with senescence in fibroblasts. Thus, enzymatic cleavage at the 3' end of the oligonucleotide maybe a step in induction of the senescence response.

Sequence identity is determined by a best fit alignment of the oligonucleotide in question with (TTAGGG)$_n$. The sequences are compared at each position, and a determination of "match" or "no match" is made at each nucleotide position, and the percent of matches, without resorting to deletion or insertion in either sequence, is the percent identity of the sequences as counted along the oligonucleotides in question. By illustration, GTTAGGG shares 100% sequence identity with (TTAGGG)$_n$. pTT shares 100% sequence identity with (TTAGGG)$_n$. (See Table 2 herein for additional examples of % identity)

Another part of the invention is a method for promoting differentiation of malignant cells in a mammal, the method comprising administering to the mammal an effective amount of a composition comprising one or more oligonucleotides which has at least 33% but less than 100% nucleotide sequence identity with (TTAGGG)$_n$. A differentiated state, can in many ways, be considered the opposite of a malignant state. Depending on the cell type, differentiation can involve the regulation of expression of a number of different genes to result in an increase or decrease in certain enzymatic activities, or cell surface proteins, for example. For example, melanocytes respond to oligonucleotides with an increase in tyrosinase expression.

In PCT/US03/11393, an association was reported between the inhibition of growth of cancer cells, caused by the cells taking up oligonucleotides with sequence identity to the telomere repeat sequence, and an increase in the appearance on the cell surface of antigens typical of differentiated cells, rather than cancer cells. Thus, a further method of the invention is to enhance the expression of one or more surface antigens indicative of differentiation of cancer cells in a mammal, said method comprising administering to the mammal an effective amount of one or more oligonucleotides as described herein, for example, one or more oligonucleotides which share at least 50% nucleotide sequence identity with the vertebrate telomere overhang repeat.

This inducement of the cells to a more differentiated state, or to take on one or more characteristics of differentiation, can be exploited in immunotherapy methods. The surface antigens associated with a differentiated state, fragments thereof, or synthetic peptides derived from the studies of the externally exposed loops of the surface antigens, can be incorporated into a vaccine to induce a cancer patient to produce cytotoxic T lymphocytes against the cells displaying the cell surface antigen. For example, in melanoma cells, the cell surface antigens MART-1, tyrosinase, TRP-1 or gp-100, or combinations thereof, can be made to increase on the cell surface when the cells take up oligonucleotides sharing at least 50% nucleotide sequence identity with the telomere overhang repeat. See Example 29 of PCT/US03/11393. These cell surface antigens can become targets for immunotherapy, for example by vaccinations with the isolated cell surface antigen or peptides having amino acid sequences derived from the surface loops of the antigens. See, for example, Jäger, E. et al., Int. J. Cancer 66:470-476, 1996; Kawakami, Y. et al., J. Immunol. 154:3961-3968, 1995; and de Vries, T. J. et al., J. Pathol. 193:13-20, 2001.

Telomerase has been a target for antiproliferative methods based on theories of using antisense oligonucleotides to bind to the RNA portion of the enzyme. However, the therapeutic methods described herein can be used independently of the presence or function of telomerase in the target cells. The telomere repeat overhang homolog pGTTAGGGTTAG (SEQ ID NO:5) was seen to bring about S-phase cell cycle arrest in normal fibroblasts and in cells of the osteosarcoma cell line Saos-2, neither of which have telomerase activity. See Examples 32 and 34 of PCT/US03/11393. Thus, for cancer cells, most of which have telomerase activity, but some of which do not, the present method can be used regardless of telomerase activity. The inhibition of growth of the cancer cells is characterized by cell cycle arrest, apoptosis, and/or differentiation to a more differentiated state. A method for inhibiting the growth of cancer cells in a mammal (e.g., human), operationally independent of the telomerase (+) or telomerase (−) state of the cancer cells, is to administer to the mammal an effective amount of a composition comprising one or more oligonucleotides which share at least 50% nucleotide sequence identity with the telomere overhang repeat.

The experiments described in Example 34 of PCT/US03/11393 demonstrate that the function of a wild type p53 protein is also not necessary to bring about the S-phase cell cycle arrest in tumors or tumor cells treated with an oligonucleotide with at least 50% sequence identity to the telomere repeat sequence. A p53-null osteosarcoma cell line was shown to respond to the addition of pGTTAGGGTTAG (SEQ ID NO:5) by arresting in S-phase. Thus, the method for inhibiting the growth of cancer cells in a mammal (e.g., human), the method including administering to the mammal an effective amount of a composition comprising one or more oligonucleotides which share at least 50% nucleotide sequence identity with the telomere overhang repeat, can be carried out whether or not the target cells have normal p53 function.

The invention further comprises a method for preventing the sequelae of exposure of the skin of a mammal to ultraviolet light—spongiosis, blistering or dyskeratosis, or any combination of these—by administering to the skin an effective amount of a composition comprising one or more oligonucleotides which share at least 50% nucleotide sequence identity with the telomere overhang repeat. The steps or steps of this method can also be used in the reduction in the incidence of skin cancer in a human, and is particularly applicable to reduce the occurrence of skin cancer in patients with xeroderma pigmentosum or other genetic predisposition to skin cancer. The method of applying to the skin an effective amount of a composition comprising one or more oligonucleotides which share at least 50% nucleotide sequence identity with the telomere overhang repeat is also a method for enhancing repair of ultraviolet irradiation-induced damage to skin.

Oxidative damage is characterized by the reaction products of reactions of molecules found in the cells with reactive oxygen species (ROS), such as hydrogen peroxide, hydroxyl radicals, and superoxide. Oxidative damage can result, for instance, from normal cellular metabolism, U.V.A irradiation, ionizing radiation, or exposure to a variety of chemicals. Reactive oxygen species can be measured in a number of ways. One assay employs a probe dichlorofluorescein diacetate (Molecular Probes, Inc.), a colorless reagent that is taken up by the cells and becomes fluorescent upon oxidation by ROS. The level of fluorescence correlates with the intracellular ROS level.

Applicants also described a method for reducing oxidative damage in a mammal, the method comprising administering to the mammal, especially to the skin of the mammal, an effective amount of a composition comprising one or more oligonucleotides which share at least 50% nucleotide sequence identity with the human telomere overhang repeat. Preferred are embodiments in which the oligonucleotide is pGAGTATGAG (SEQ ID NO:1). See results in Examples 15, 21, 22, 23 and 52 of PCT/US03/11393 suggesting that oligonucleotide treatment enhances the ability of cells to repair oxidative DNA damage.

Applicants have further described a method for treating melanoma in a mammal, comprising administering to the human an effective amount of a composition comprising one or more oligonucleotides that share at least 50% nucleotide sequence identity with the human telomere overhang repeat. In particular cases, the oligonucleotide can be pGTTAGGGT-TAG (SEQ ID NO:5); pTT can also be used in the method. Applicants have shown the effectiveness of oligonucleotide therapy using human melanoma cells in a mouse model. See PCT/US03/11393 Examples 30, 49, 50 and 51 and Example 9 set out below.

Another aspect of the invention concerns a method for reducing proliferation of keratinocytes in the skin of a human, in which the method comprises applying to the skin an effective amount of a composition comprising one or more oligonucleotides that share at least 50% nucleotide sequence identity with the human telomere overhang repeat. The method is applicable to disorders of the skin characterized by proliferation of keratinocytes in the skin, such as seborrheic keratosis, actinic keratosis, Bowen's disease, squamous cell carcinoma or basal cell carcinoma. pTT is effective in the method.

The present invention includes the method of treating a disease or disorder in a mammal, wherein the disease or disorder is characterized by abnormal proliferation of cells, including, but not limited to, solid tumors, blood-cell related tumors (e.g., leukemias), tumor metastases, benign tumors (e.g., hemangiomas, acoustic neuromas, neurofibromas, trachomas, and pyogenic granulomas), including those in which cells are immortalized such as apudoma, choristoma, branchioma, malignant carcinoid syndrome, carcinoid heart disease, carcinoma, (e.g., Walker, basal cell, basosquamous, Brown-Pearce, ductal, Ehrlich tumor, in situ, Krebs 2, merkel cell, mucinous, non-small cell lung, oat cell, papillary, schirrhous, bronchiolar, bronchogenic, squamous cell, and transitional cell), histiocytic disorders, leukemia (e.g., b-cell, mixed cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, hystiocytoma, lipoma, liposacaroma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblatoma, cementoma, odontoma, teratoma, thymoma, throphoblastic tumor, adenocarinoma, adenoma, cholangioma, cholesteatoma, cyldindroma, cystadenocarcinoma, cystadenoma, garnulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myoscarcoma, rhabdomyoma, rhabdomyosarcoma, ependymoma, neuroblastoma, neuroepithelioma, neurofirbroma, neuroma, paraganglioma, paraganglioma nonchromaffin, antiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinoscarcoma, chondrosarcoma, cytosarcoma phyllodes, fibrosarcoma, hemangiosarcoma, leiomyosarcoma, leukosarcoma, liposcarcoma, lymphangiosarcoma, myoscarcoma, myxosarcoma, ovarian carcinoma, rhabdomyosarcoma, sarcoma (e.g., Ewing's experiemental, Kaposi's, and mast-cell), neoplasms (e.g., bone, breast, digestive system, colorectal liver, pancreastic, pituitary, testicular, orbital, head and neck, central nervous system acoustic, pelvic, respiratory tract, and urogenital), neurofibromatosis, and cervical dysplasia), and for treatment of other conditions in which cells have increased proliferation. Hyperproliferative disorders can also be those characterized by excessive or abnormal stimulation of fibroblasts, such as scleroderma, and hypertrophic scars (i.e., keloids).

The oligonucleotide or oligonucleotides to be used in therapies to alleviate hyperproliferative disorders such as cancer can be used in a composition in combination with a pharmaceutically or physiologically acceptable carrier. Such a composition may also contain in addition, diluents, fillers, salts, buffers, stabilizers, solubilizers, and other materials well known in the art. Cationic lipids such as DOTAP [N-(2, 3-dioleoyloxy)propyl]-N,N,N-trimethylammonium salts may be used with oligonucleotides to enhance stability. Oligonucleotides may be complexed with PLGA/PLA copolymers, chitosan or fumaric acid/sebacic acid copolymers for improved bioavailability {where PLGA is [poly(lactide-co-glycolide)]; PLA is poly(L-lactide)}. The terms "pharmaceutically acceptable" and "physiologically acceptable" mean a non-toxic material that does not interfere with the effectiveness of the biological activity of the active ingredient(s). The characteristics of the carrier will depend on the route of administration.

A composition to be used as an antiproliferative agent may further contain other agents which either enhance the activity of the oligonucleotide(s) or complement its activity or use in treatment, such as chemotherapeutic or radioactive agents. Such additional factors and/or agents may be included in the composition to produce a synergistic effect with the oligonucleotide(s), or to minimize side effects. Additionally, administration of the composition of the present invention may be administered concurrently with other therapies, e.g., administered in conjunction with a chemotherapy or radiation therapy regimen.

The oligonucleotides as described herein can be used in combination with other compositions and procedures for the treatment of diseases. For example, a tumor may be treated conventionally with surgery, radiation, chemotherapy, or immunotherapy, combined with oligonucleotide therapy, and then oligonucleotides may be subsequently administered to the patient to extend the dormancy of micrometastases and to stabilize and inhibit the growth of any residual primary tumor.

The compositions of the present invention can be in the form of a liposome in which oligonucleotide(s) of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like.

Pharmaceutical compositions can be made containing oligonucleotides to be used in antiproliferative therapy. Administration of such pharmaceutical compositions can be carried out in a variety of conventional ways known to those of ordinary skill in the art, such as oral ingestion, inhalation, for example, of an aerosol, topical or transdermal application, or intracranial, intracerebroventricular, intracerebral, intravaginal, intrauterine, oral, rectal or parenteral (e.g., intravenous, intraspinal, subcutaneous or intramuscular) route, or cutaneous, subcutaneous, intraperitoneal, parenteral or intravenous injection. The route of administration can be determined according to the site of the tumor, growth or lesion to be targeted.

To deliver a composition comprising an effective amount of one or more oligonucleotides to the site of a growth or tumor, direct injection into the site can be used. Alternatively, for accessible mucosal sites, ballistic delivery, by coating the oligonucleotides onto beads of micrometer diameter, or by intraoral jet injection device, can be used.

Viral vectors for the delivery of DNA in gene therapy have been the subject of investigation for a number of years. Retrovirus, adenovirus, adenoassociated virus, vaccinia virus and plant-specific viruses can be used as systems to package and deliver oligonucleotides for the treatment of cancer or other growths. Adeno-associated virus vectors have been developed that cannot replicate, but retain the ability to infect cells. An advantage is low immunogenicity, allowing repeated administration. Delivery systems have been reviewed, for example, in Page, D. T. and S. Cudmore, *Drug Discovery Today* 6:92-1010, 2001.

Studies carried out using oligonucleotides on the theory of their inhibiting the function of a target nucleic acid (antisense oligonucleotides), most of these studies carried out with phosphorothioate oligonucleotides, have found effective methods of delivery to target cells. Antisense oligonucleotides in clinical trials have been administered in saline solutions without special delivery vehicles (reviewed in Hogrefe, R. I., Antisense and Nucleic Acid Drug Development 9:351-357, 1999).

Formulations suitable for parenteral administration include aqueous and non-aqueous sterile injection solutions which may contain anti-oxidants, buffers, bacteriostats and solutes which render the formulation isotonic with the fluids of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. A preferred pharmaceutical composition for intravenous, cutaneous, or subcutaneous injection should contain, in addition to oligonucleotide(s) of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

Use of timed release or sustained release delivery systems are also included in the invention. Such systems are highly desirable in situations where surgery is difficult or impossible, e.g., patients debilitated by age or the disease course itself, or where the risk-benefit analysis dictates control over cure. One method is to use an implantable pump to deliver measured doses of the formulation over a period of time, for example, at the site of a tumor.

A sustained-release matrix can be used as a method of delivery of a pharmaceutical composition comprising oligonucleotides, especially for local treatment of a growth or tumor. It is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

Also encompassed by the present invention is combination therapies in in which one or more oligonucleotides of the present inention are administered in combination with other therapies. For example, patients may receive suboptional doses of both an oligonucleotide of the present invention along with suboptional doses of a chemotherapeutic agent such as vincristin or doxyrubicin—the combination of which has been shown to induce apoptosis in malignant B-cells.

The amount of oligonucleotide of the present invention in the pharmaceutical composition of the present invention will depend upon the nature and severity of the condition being treated, and on the nature of prior treatments which the patient has undergone. For a human patient, the attending physician will decide the dose of oligonucleotide of the present invention with which to treat each individual patient. Initially, the attending physician can administer low doses and observe the patient's response. Larger doses may be administered until the optimal therapeutic effect is obtained for the patient, and at that point the dosage is not increased further. The duration of therapy using the pharmaceutical composition of the present invention will vary, depending on the severity of the disease being treated and the condition and potential idiosyncratic response of each individual patient.

It is apparent from the data disclosed herein including data in applications and patents incorporated herein by reference that the oligonucleotides of the present invention have pleiotropic effects on gene expression in tumor cells (e.g., MART-1, tyrosinase, TRP-1 or gp-100 and others). Based on these pleiotropic effects in cancer cells, the oligonucleotides of the present invention can be said to induce in those cells an "anticancer expression profile" all or some of which may be further exploited as possible targets for anti-cancer intervention.

The invention is further illustrated by the following non-limiting Examples.

EXAMPLES

Example 1

Based on our observation that the oligonucleotides of the present invention have the same relative molar efficacy in causing pigmentation in melanocytes, apoptosis and cellular senescence in malignant cells, a retrospective comparison of activities of a number of oligonucleotides was made and the relative molar efficacy of the oligonucleotides with respect to one another was calculated with the results set out in Table 1. Based on these results, we have concluded that the following parameters are among those that are important in determining efficacy of the oligonucleotides of the present invention.

1) percent tolemere identity;
2) number of hydrolyzable linkages;
3) guanine content;
4) sequence motif The comparisons also reveal that the presence of cytosine residues in the oligonucleotides can have a negative impact on molar efficiency.

TABLE 1

Relative Molar Efficacy of Tested T-Oligos

| Sequence | | Activity |
|---|---|---|
| T | | 0 |
| * TT | | 1 |
| AA | | 0 |
| TTA | | 1.5 |
| TTAG | | 2 |
| * GAGTATGAG | (SEQ ID NO: 37) | 3 |
| AGTATGA | | 2 |
| GTATG | | 1.5 |
| CATAC | | 0 |
| GCATGCATGCATTACGTACG | (SEQ ID NO: 38) | 0 |
| GTTAGGGTTAG | (SEQ ID NO: 2) | 6 |
| CTAACCCTAAC | (SEQ ID NO: 3) | 0 |
| GTACGTACGTA | (SEQ ID NO: 4) | 0 |
| TTAGGG | (SEQ ID NO: 6) | 3 |
| TTCGGG | (SEQ ID NO: 7) | 0 |
| CTAGGG | (SEQ ID NO: 8) | 0.5 |
| TTAGGC | (SEQ ID NO: 9) | 0.5 |
| GGTAGGTGTAGGATT | (SEQ ID NO: 10) | 8 |
| GGTAGGTGTAGGTTA | (SEQ ID NO: 11) | 7 |
| GGTTAGGTGTAGGTT | (SEQ ID NO: 12) | 7 |
| GGTTAGGTGGAGGTTT | (SEQ ID NO: 13) | 8 |
| GGTTAGGTGTAGGTTT | (SEQ ID NO: 14) | 10 |
| GGTTAGGTTAGGTTA | (SEQ ID NO: 15) | 7 |
| GTTAGGGTTAG | (SEQ ID NO: 5) | 6 |
| GGTAGGTGTAGGGTG | (SEQ ID NO: 16) | 9 |
| GTTAGGGTT | (SEQ ID NO: 17) | 6 |
| TTAGGGTTA | (SEQ ID NO: 18) | 4 |
| GTTAGGTTTAAGGTT | (SEQ ID NO: 19) | 6 |
| GGTCGGTGTCGGGTG | (SEQ ID NO: 20) | 1 |
| GGCAGGCGCAGGGCG | (SEQ ID NO: 21) | 1 |
| GTTAGGGTTAGGGTT | (SEQ ID NO: 22) | 8 |
| GGGTTAGGG | (SEQ ID NO: 23) | 7 |
| $G_sT_sT_sA_sG_sG_sG_sT_sT_sA_sG$ | (SEQ ID NO: 24) | 0 |
| $G_sT_sTAGGGTT_sA_sG$ | (SEQ ID NO: 25) | 1 |
| $GTTAGGGTT_sA_sG$ | (SEQ ID NO: 26) | 2 |
| $G_sT_sTAGGGTTAG$ | (SEQ ID NO: 27) | 3 |

Note:
All sequences have a 5' phosphate group, and all have phosphodiester linkage unless otherwise indicated: $x_sx$ = phosphorothioate linkage.
* Tested without the 5' phosphate group: no activity (no uptake).

Example 2

Sequence Parameters

In order to further examine the effect of various nucleotide sequence parameters on the relative efficacy of T-oligos to induce apoptosis in MM-AN melanoma several oligonucleotides were synthesized which had varying % identity with the telomere repeat and which were varied with respect to the number of bases, number of guanine bases, number of GT's, number of GGT's, and the number of GGTTs. Apoptosis studies were undertaken as described in PCT/US03/11393 incorporated herein by reference. (See e.g. Examples 13, 28) MM-An melanoma cells were exposed to each of the T-oligos shown in Table 3 at a concentration of 40 µM for 96 hours. After 96 hours the cells were stained with propidium iodide and the percent of DNA content in the sub GI portion of the cell cycle was determined by FACS analysis. Relative activity was determined by comparison to the relative activities shown in Table 1. The sequence parameters that were investigated include: % identity with the telomere repeat sequence $(TTAGGG)_n$; the number of bases, the number of guanine residues and the presence or absence of various sequence motifs including the number of GTs, GGTs, and GGTTs.

The most active T-oligo in this study was shown to be GGTTGGTTGGTTGGTT, (SEQ ID NO:29) which was 56% identical to the $(TTAGGG)_n$ telomere repeat has 16 bases 8 guanine residues, four GT sequences, four GGTs and four GGTTS and which showed relative activity of 12. Typically, GGTTGGTTGGTTGGTT (SEQ ID NO:29) had relative activity of 12 yielding 61% apoptotic cells compared to 43%-47% apoptotic cells seen with oligonucleotides having a relative activity of 10 while GTTAGGGTTAG (SEQ ID NO:5) with a relative activity of 6 yielded 25% apoptotic cells in the assay. Notably, the sequence GGAGGAGGAGGAGGA (SEQ ID NO:31) which was 47% identical to the telomere repeat has 10 G residues but which lacked any GT, GOT, or GGTT repeats had no activity in this assay. Of additional note is the fact that the T-oligo TGTGGTTGTGGTGTGG (SEQ ID NO:33) which is 15 bases in length, only 40% identical to the telomere repeat, has 9 Gs, 5 GTs, and 2 GGTTs has a relative molar efficacy of 10. The T-oligo TAGTGTTAGGTGTAG (SEQ ID NO:34) which is 15 bases in length only 40% identical to the telomere repeat has 6 Gs 4 GTs and 1 GGT and has a relative molar efficacy of 10.

TABLE 2

| Sequence | Relative Activity | % Identity | # Bases | #G | #GT | #GGT | #GGTT |
|---|---|---|---|---|---|---|---|
| GTTAGGGTTAG (SEQ ID NO: 5) | 6 | 100 | 11 | 5 | 2 | 1 | 1 |
| GGTTAGGGTGTAGGTTT (SEQ ID NO: 28) | 10 | 81 | 16 | 7 | 4 | 3 | 2 |
| GGTTGGTTGGTTGGTT (SEQ ID NO: 29) | 12 | 56 | 16 | 8 | 4 | 4 | 4 |
| GGTGGTGGTGGTGGT (SEQ ID NO: 30) | 10 | 60 | 15 | 10 | 4 | 4 | 0 |
| GGAGGAGGAGGAGGA (SEQ ID NO: 31) | 0 | 47 | 15 | 10 | 0 | 0 | 0 |
| GGTGTGGTGTGGTG (SEQ ID NO: 32) | 10 | 60 | 15 | 9 | 6 | 3 | 0 |
| TGTGGTGTGGTGTGG (SEQ ID NO: 33) | 10 | 40 | 15 | 9 | 5 | 2 | 0 |
| TAGTGTTAGGTGTAG (SEQ ID NO: 34) | 9 | 40 | 15 | 6 | 4 | 1 | 0 |

Example 3

Dose-Response Effects of T-Oligos on Apoptosis in MM-AN Cells

Figure 4:
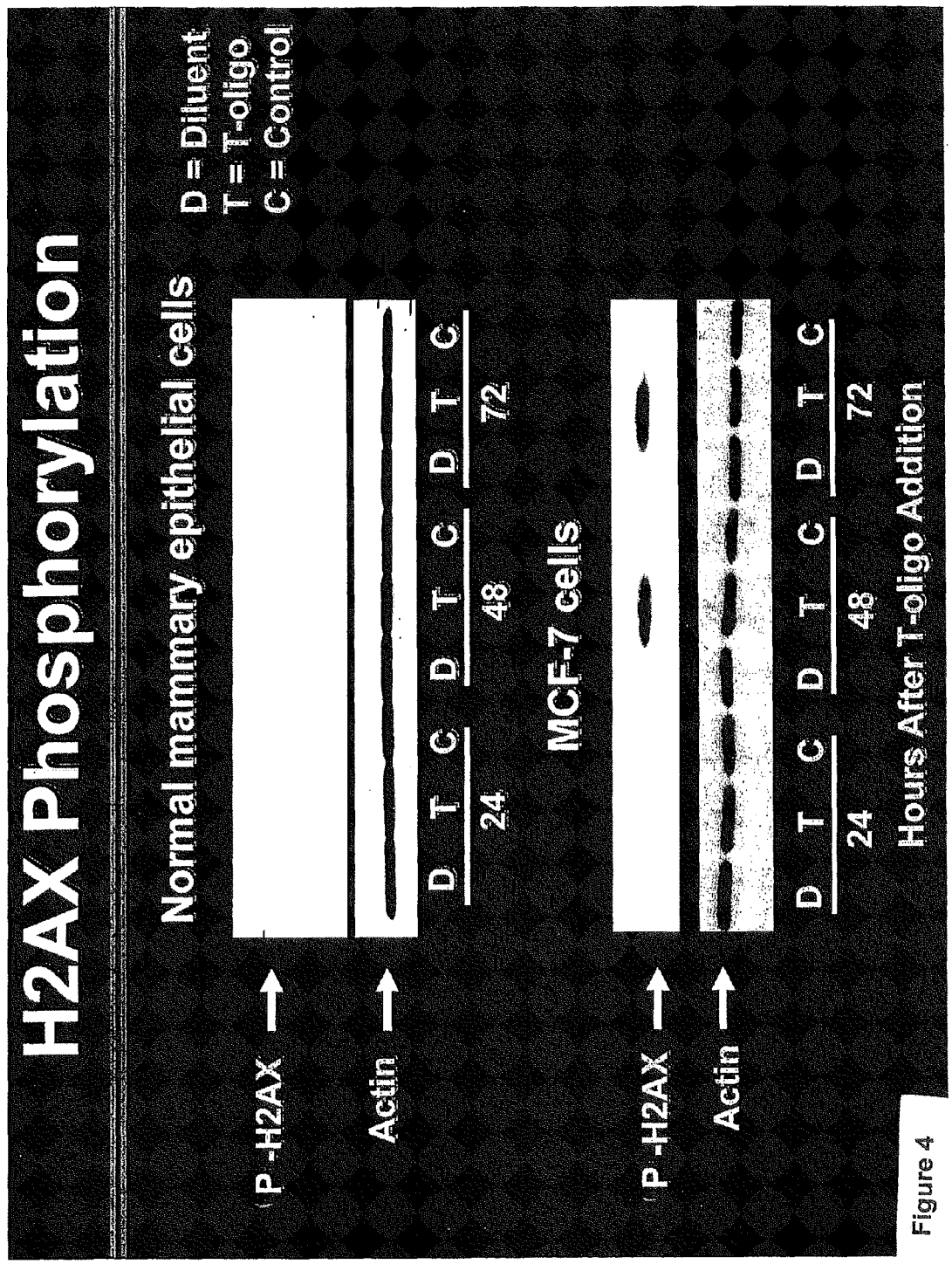
FIG. 4—Induction of phosphorylation of H2AX in normal mammary epithelial cells and MCF-7 breast tumor cells.

Experiments were conducted comparing the ability of different T-oligos at a range of concentrations to induce apoptosis in MM-AN melanoma cells. Apoptosis studies were undertaken as described in PCT/US03/11393 (See e.g. Examples 13 and 28) and treated once in triplicate with each T-oligo at each dose (1, 5 and 10 µM) and subjected to FACS analysis after 96 hours as described in PCT/US03/11393. The T-oligos used were pGTTAGGGTTAG (SEQ ID NO:5), p(GGTT)$_4$ (SEQ ID NO:29) and p(GGTT)$_5$ (SEQ ID NO:35). Results are shown in FIGS. 1 and 4. The results are compatible with earlier experiments and show that the standard (GTTAGGGTTAG) (SEQ ID NO:5) is less effective at inducing apoptosis than either the p(GGTT)$_4$ (SEQ ID NO:29) or p(GGTT)$_5$ (SEQ ID NO: 35), which were comparable in efficacy. In a separate experiment (GGTT)$_4$ (SEQ ID NO:29) with and without 5' phosphorylation were equally active in the MM-AN cell assay for apoptosis. Maximally effective doses for both the p(GGTT)$_4$ (SEQ ID NO:29) and p(GGTT)$_5$, (SEQ ID NO:35) as determined in other experiments was determined to be 20 µM.

Example 4

Apoptosis and H2AX Phosphorylation

Figure 2:
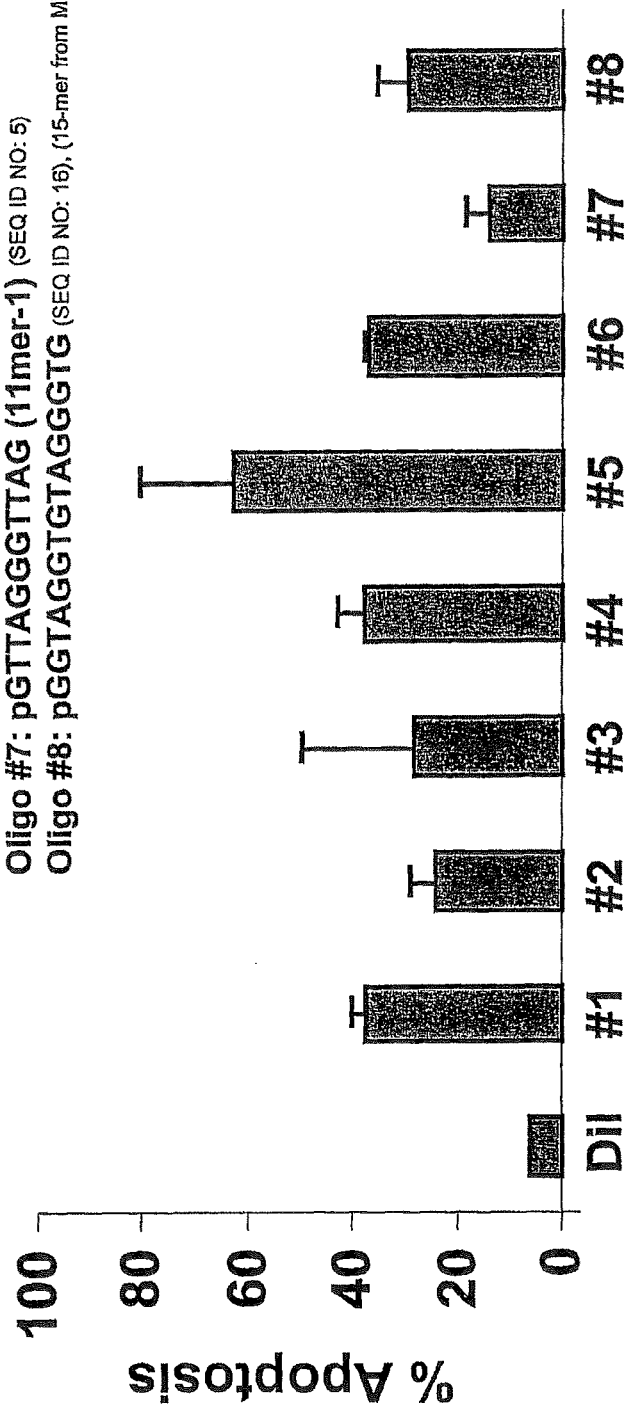
FIG. 2—Induction of apoptosis in MM-AN cells by various oligonucleotides.

Experiments were conducted to examine the ability of various oligonucleotides, to induce apoptosis in MM-AN cells and to determine their effects on phosphorylation of histone H2AX in MCF7 cells, a breast cancer cell line. The apoptosis data was obtained using methods set and in Examples 13 and 28 of PCT/US03/11393 are from a FACS analysis (% cells with <2N DNA content) in duplicate dishes with moderate variability. Data is shown in FIG. 2. These data indicate that all of the tested oligonucleotides are comparably active to the previously tested 15-mer (SEQ ID NO:34) and more active than the standard 11-mer (SEQ ID NO:5).

Figure 3:
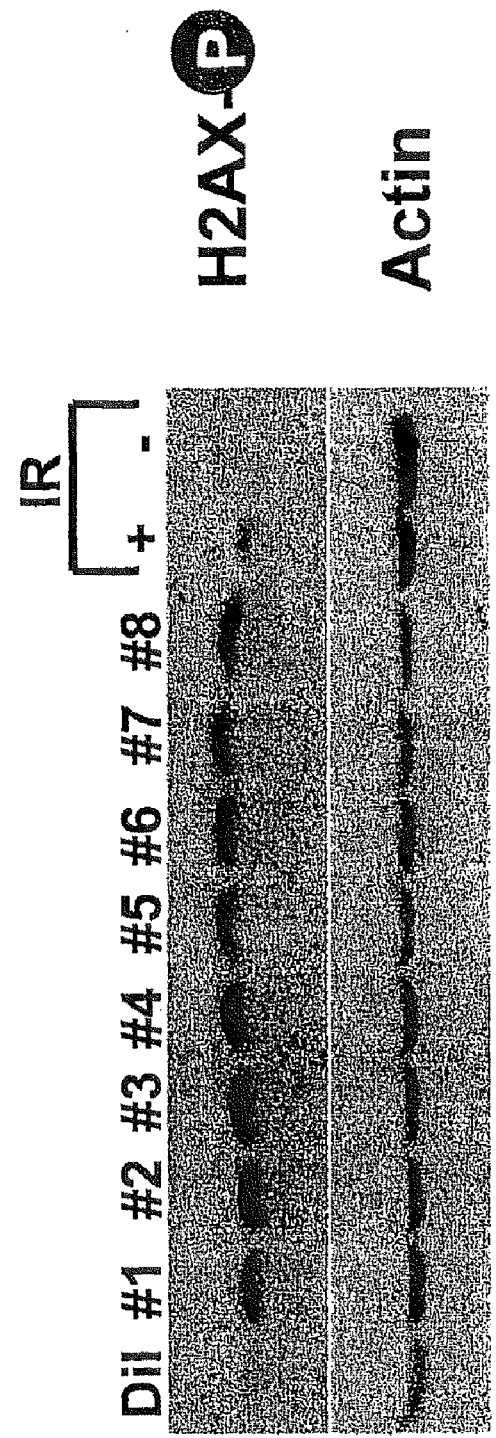
FIG. 3—Induction of phosphorylation of H2AX by various oligonucleotides.

H2AX phosphorylation results are shown in FIG. 3 and indicate that the oligonucleotides are capable of inducing phosphorylation of H2AX in MCF-7 cells.

Example 5

The Effects of T-oligos on Phosphorylation of H2AX and p53

Figure 5:
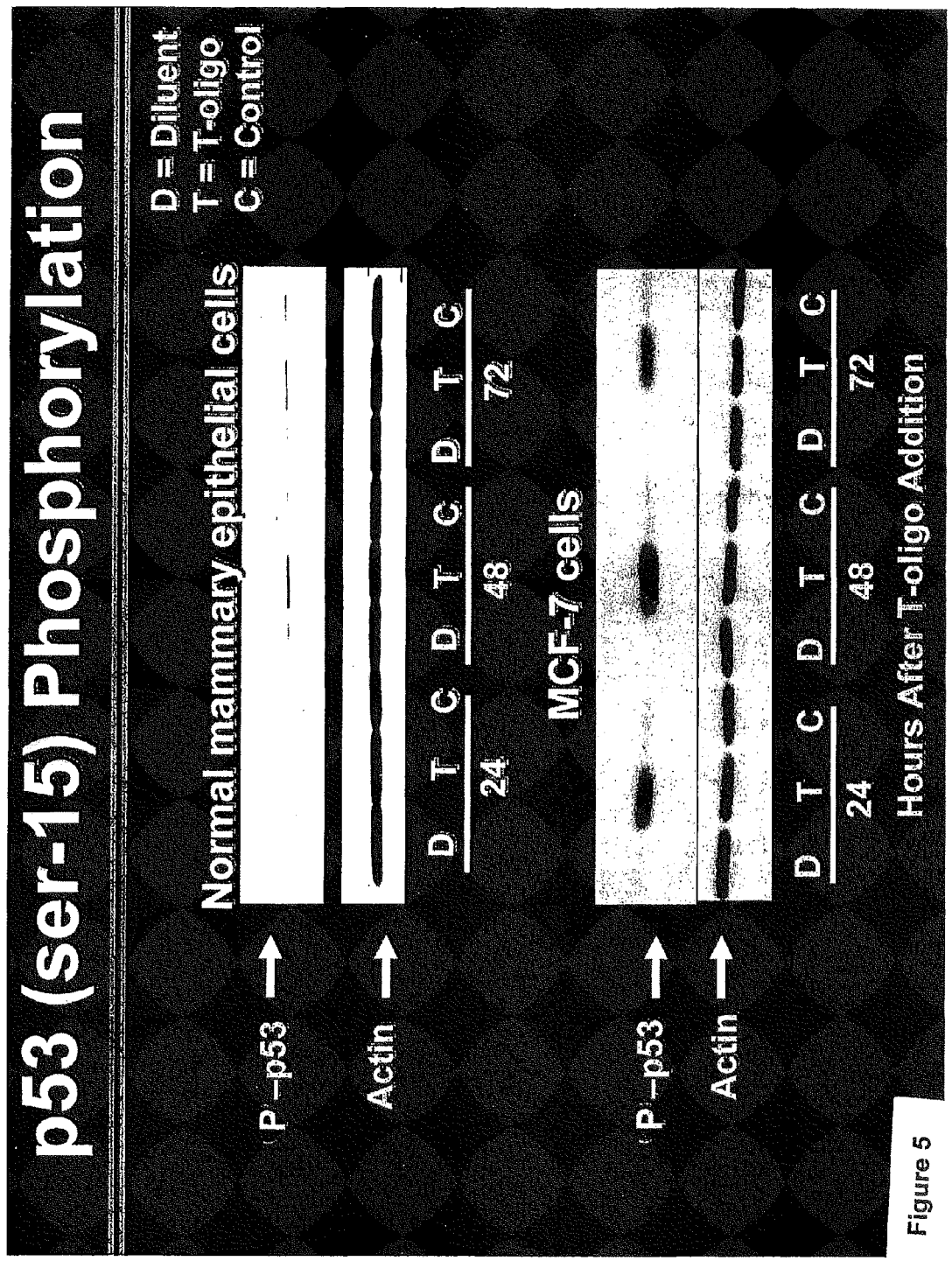
FIG. 5—Induction of phosphorylation of p53 in normal mammary epithelial cells and MCF-7 breast tumor cells FIG. 6—Effect of oligonucleotides on growth of normal mammary epithelial cells.
Figure 6:
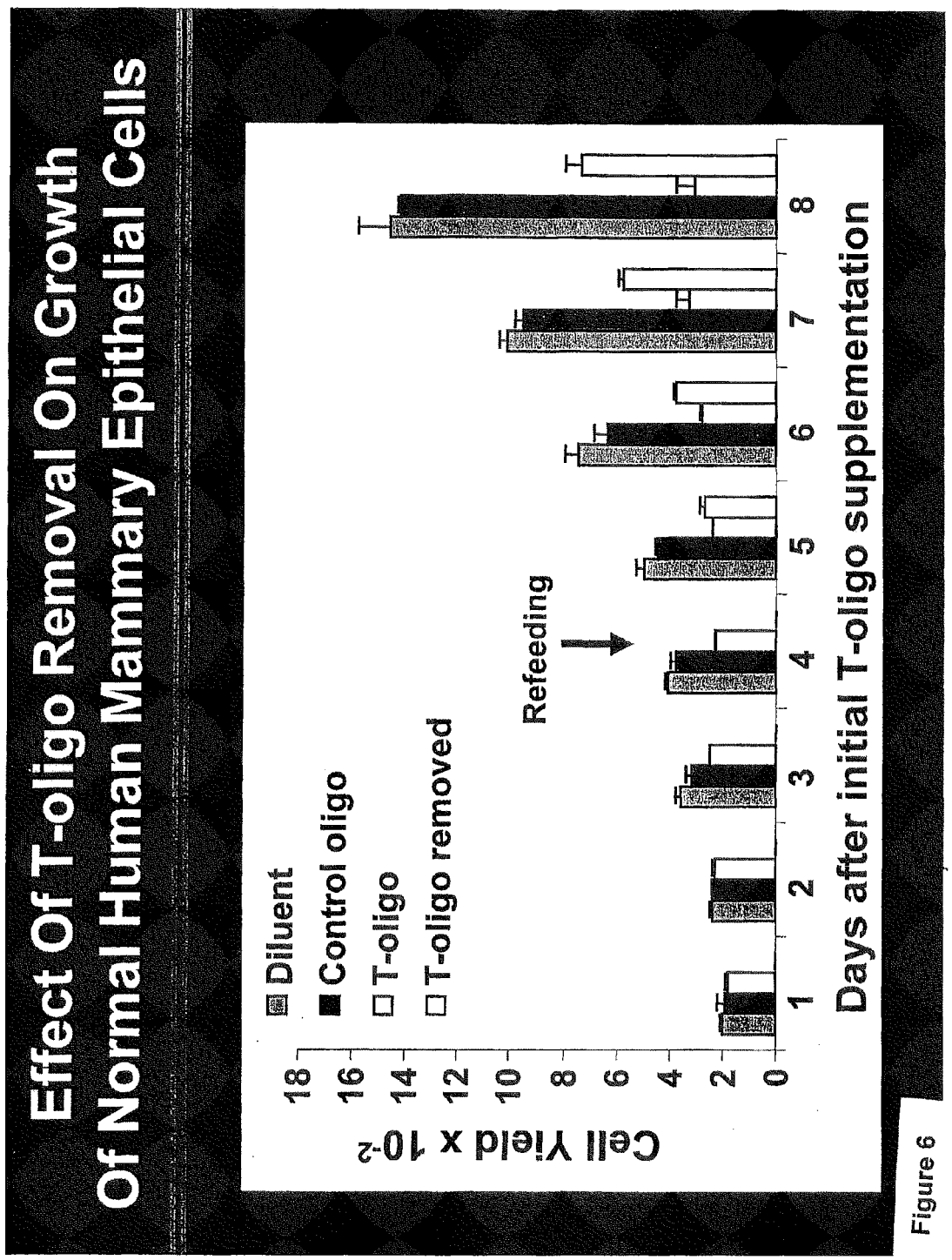
Figure 7:
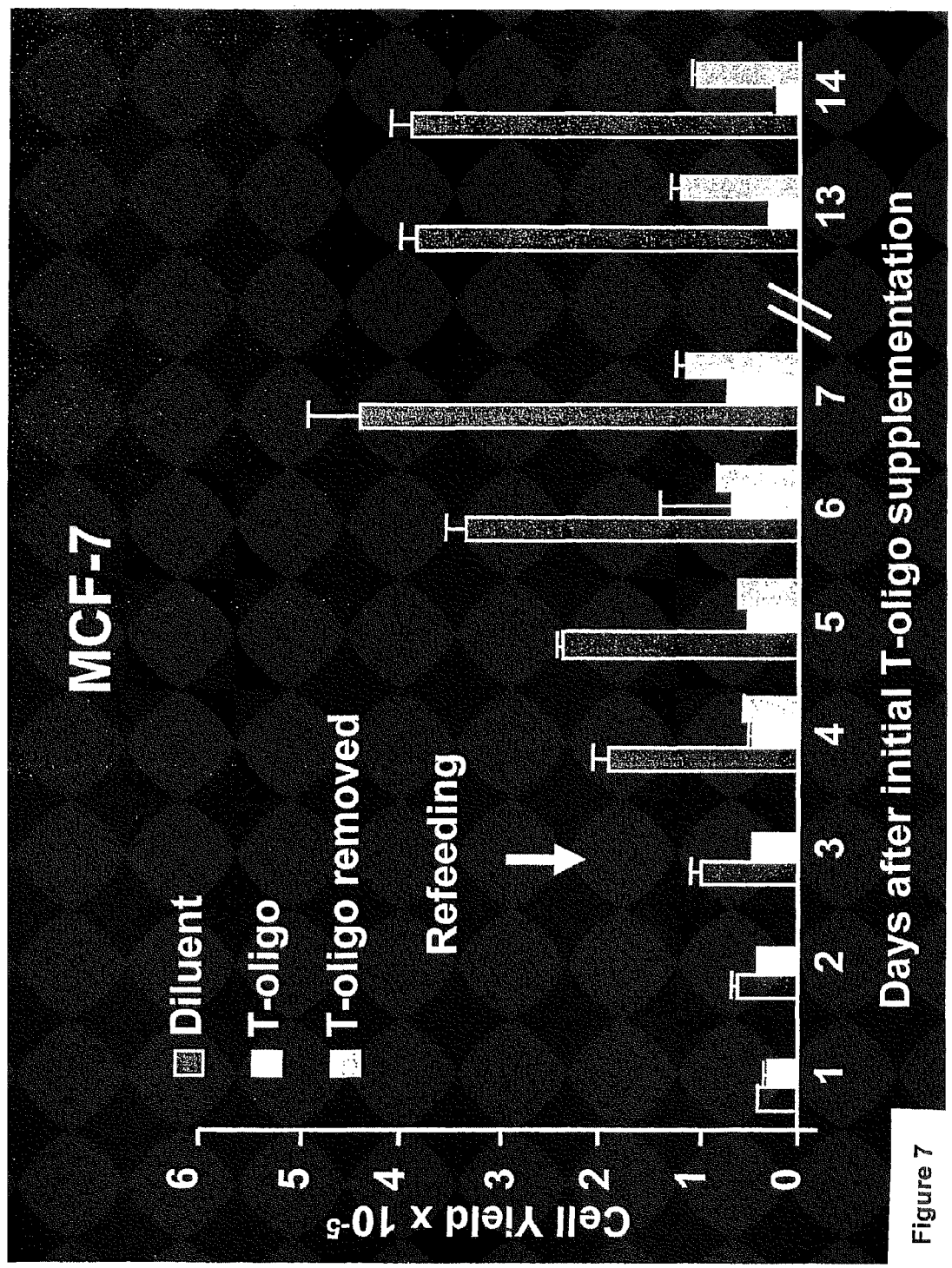
FIG. 7—Effect of oligonucleotides on growth of MCF-7 breast tumor cells.
Figure 8:
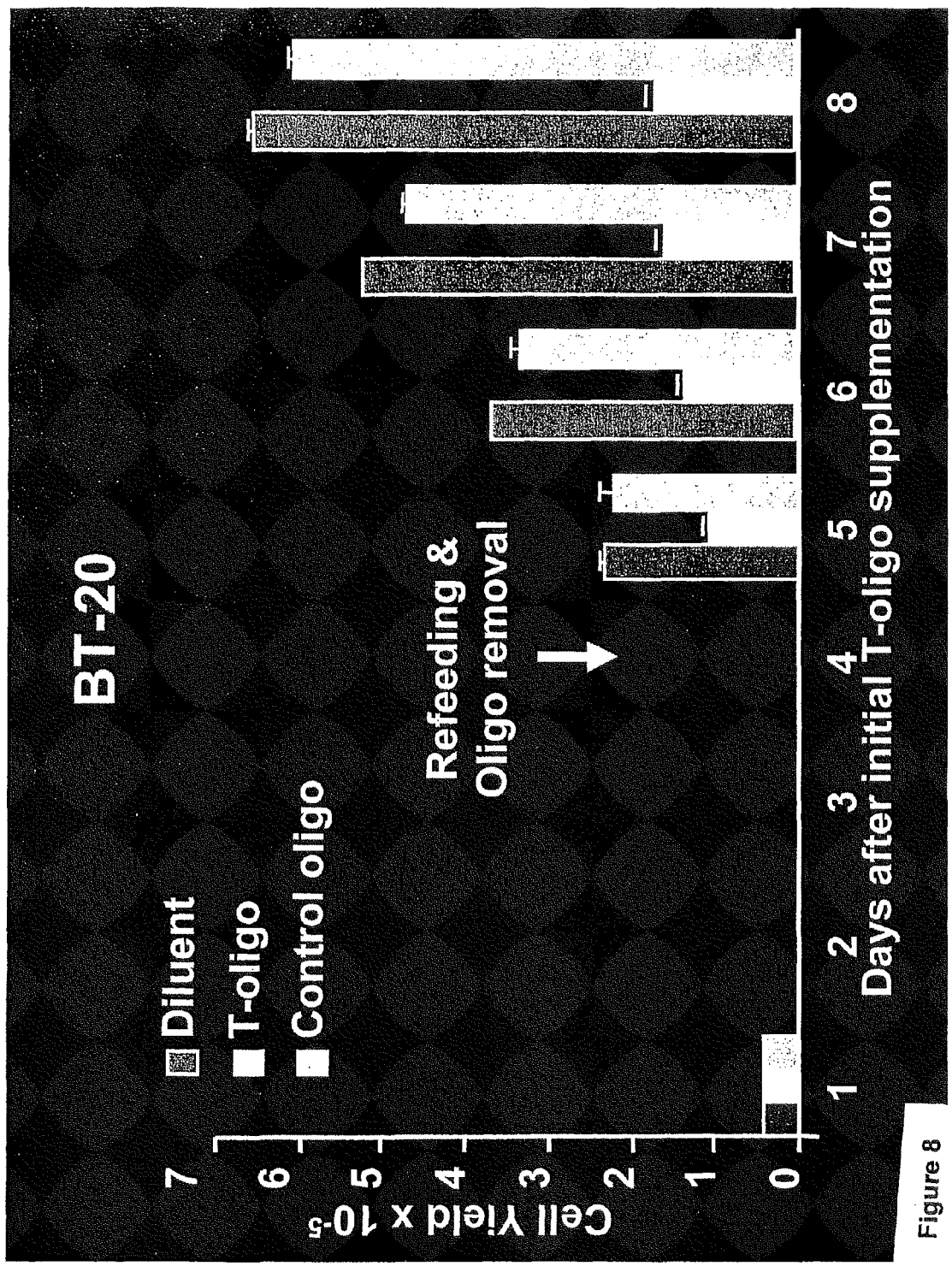
FIG. 8—Effect of oligonucleotides on growth of BT20 breast tumor cells.

Additional studies were conducted to assess the ability of certain T-oligos to phosphorylate the DNA damage response protein histone H2AX and p53 in human breast cancer cells. Cells were treated with the GTTAGGGTTAG (SEQ ID NO:5) at (40 µm), its complement or diluent and resulting phosphorylation of histone H2AX and p53 as measured by western blot analysis and apoptosis of breast cancer cells was assayed. The results of this study indicate that (pGTTAGGGTTAG) (SEQ ID NO:5) versus complimentary control T-oligo or diluent alone strongly induces phosphorylation of H2AX and p53 in human breast cancer (MCF-7) cells (see FIGS. 4 and 5) but only very weakly induces these phosphorylations in normal human mammary epithelial cells. Similarly, GTTAGGGTTAG (SEQ ID NO:5) strongly induces apoptosis in MCF-7 and BT-20 breast carcinoma (measured as described above) cells but only very weakly induces apoptosis in normal mammary epithelial cells (data not shown). A single supplementation of MCF-7 or BT-20 cells on day zero causes permanent growth arrest (at least through 14 or 8 days respectively), even when the cells are re-fed with serum containing fresh medium that lacks the oligonucleotide; while the same supplementation of normal mammary epithelial cells on day zero arrests their growth through day 4, but upon re-feeding with fresh medium, the cells again begin to grow at a doubling rate comparable to that of the diluent treated control cells. (FIGS. 6 and 7)

Example 6

Effect of T-oligos on Survival of Mice Infected with Human Breast Cancer Cells

Figure 9:
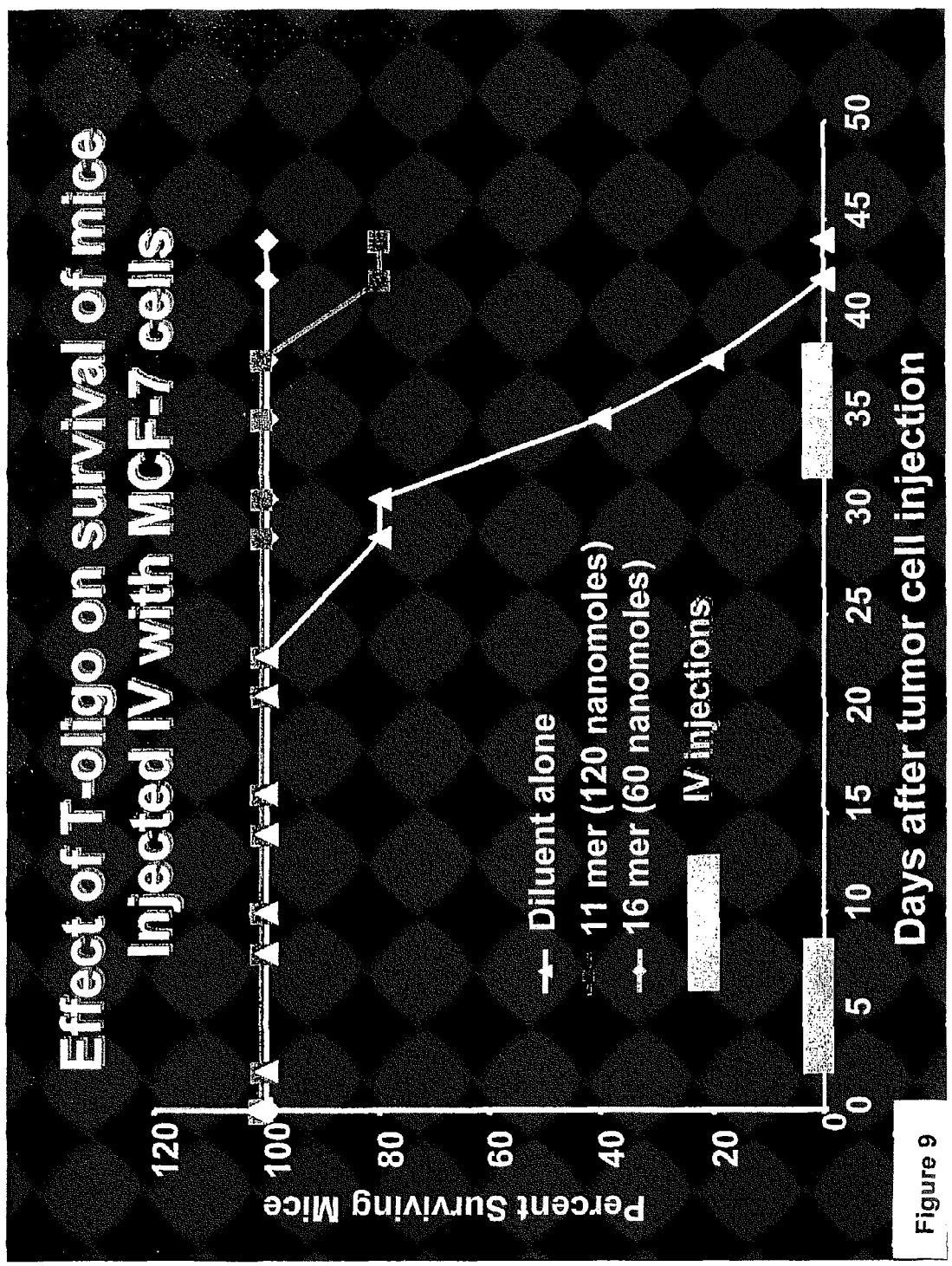
FIG. 9—Effect of oligonucleotides on survival of mice injected with MCF-7 breast cancer cells.

Animals were injected in the tail vein with MCF-7 cells at a dosage which results in death of all the injected mice within about 42 days. Mice were treated with diluent alone with 60 nmoles or 120 nmoles of pGTTAGGGTTAG (SEQ ID NO:5) with pGGTTAGGTTTAGGTTT (SEQ ID NO:36) and 10 μM and 20 μM, compared to diluent (saline) alone. The results are shown in FIG. 9 which shows that both T-oligos greatly prolong survival of mice that have received tail vein injections of MCF-7 cells with the 16 mer being more effective than the 11 mer.

Example 7

Effects of T-oligos on Squamous Cell Carcinoma in Mice

Figure 10:
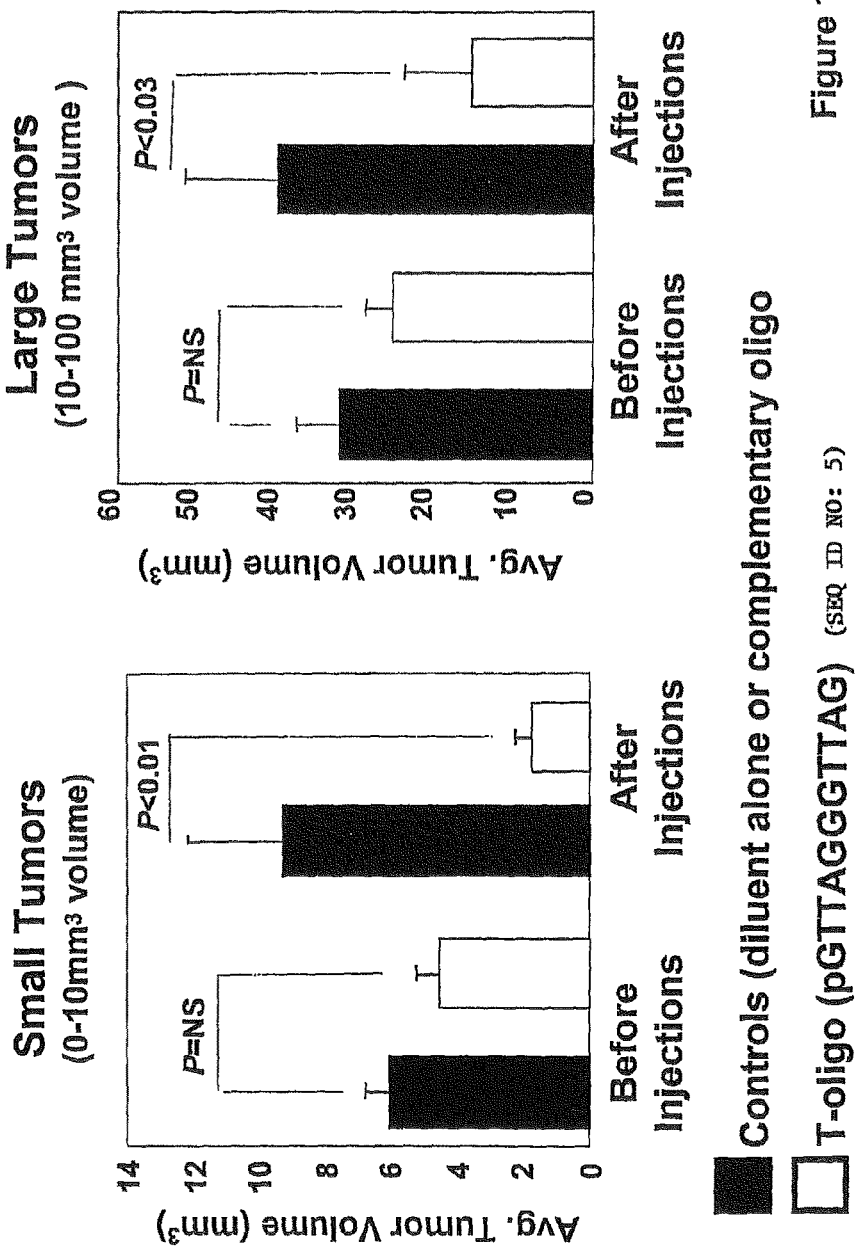
FIG. 10—Effect of intratumoral injection oligonucleotides on squamous cell carcinoma in mice.

XPA KO mice lacking the XPA DNA repair protein were irradiated twice weekly with 6 mJ/cm$^2$ of U.V.B until squamous cells tumor developed. Tumors were then injected three times weekly with 40 μM, GTTAGGGTTAG (SEQ ID NO:5), 10-40 μl per injection depending on tumor size. The results of this study shown in FIG. 10 indicates that aggressively growing squamous cell carcinoma can regress substantially or completely as a result of treatment with GTTAGGGTTAG (SEQ ID NO:5).

Example 8

Effects of T-oligos on Growth of MM-AN Melanoma Cells in Mice SCID Mice

Figure 11:
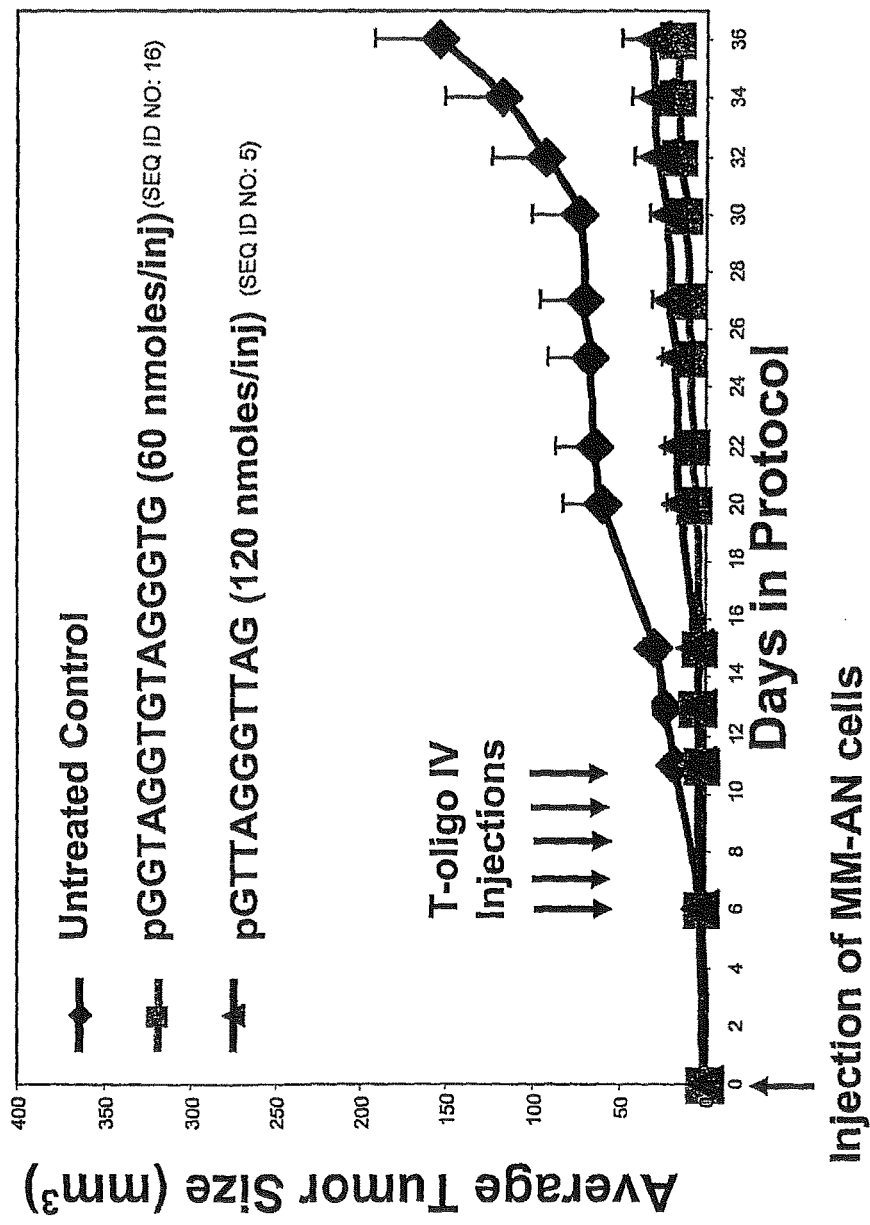
FIG. 11—Effect of oligonucleotides on MM-AN melanoma in SCID mice.
Figure 12:
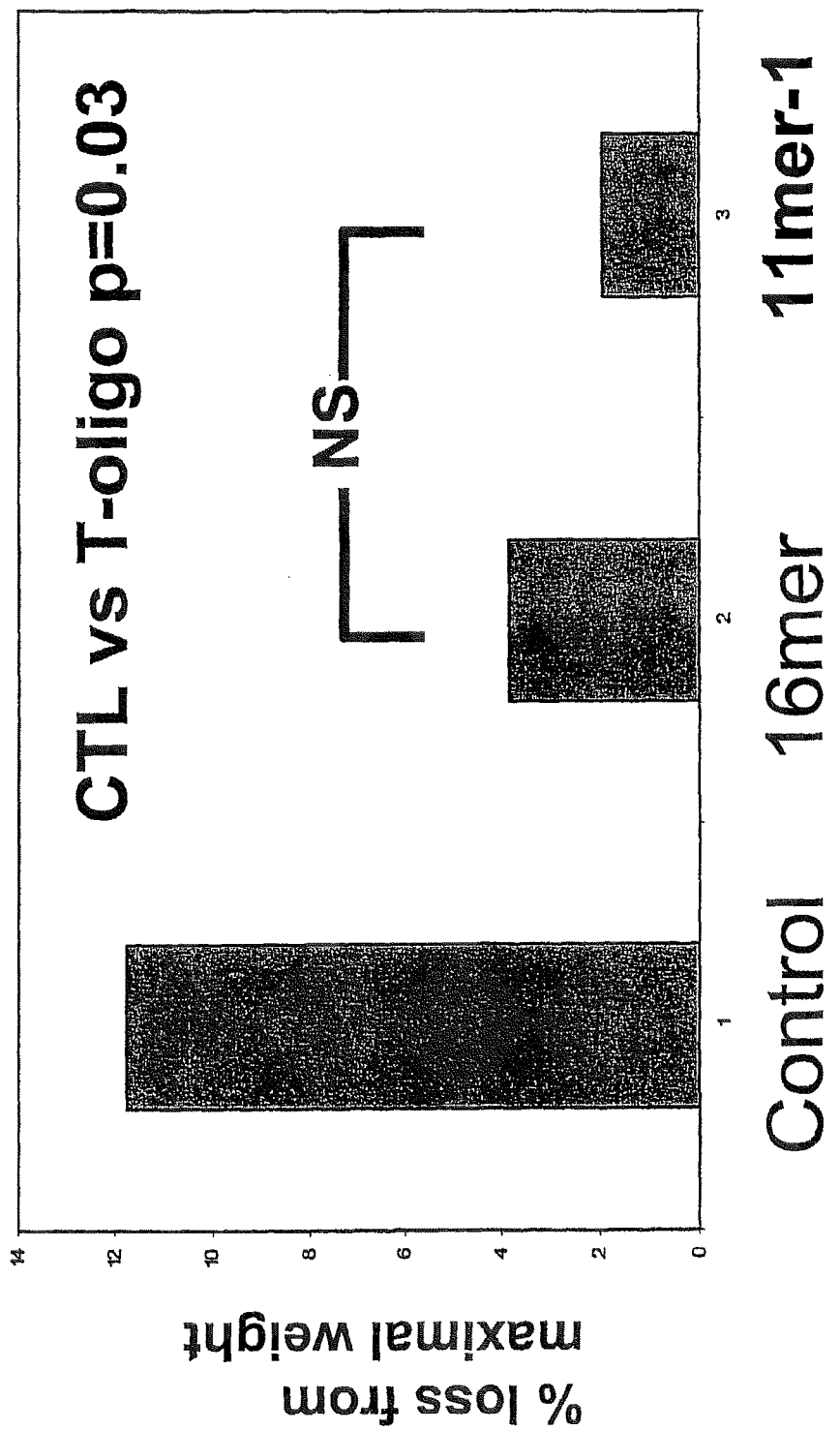
FIG. 12—Effect of oligonucleotides on weight loss in SCID mice with melanoma.
Figure 13:
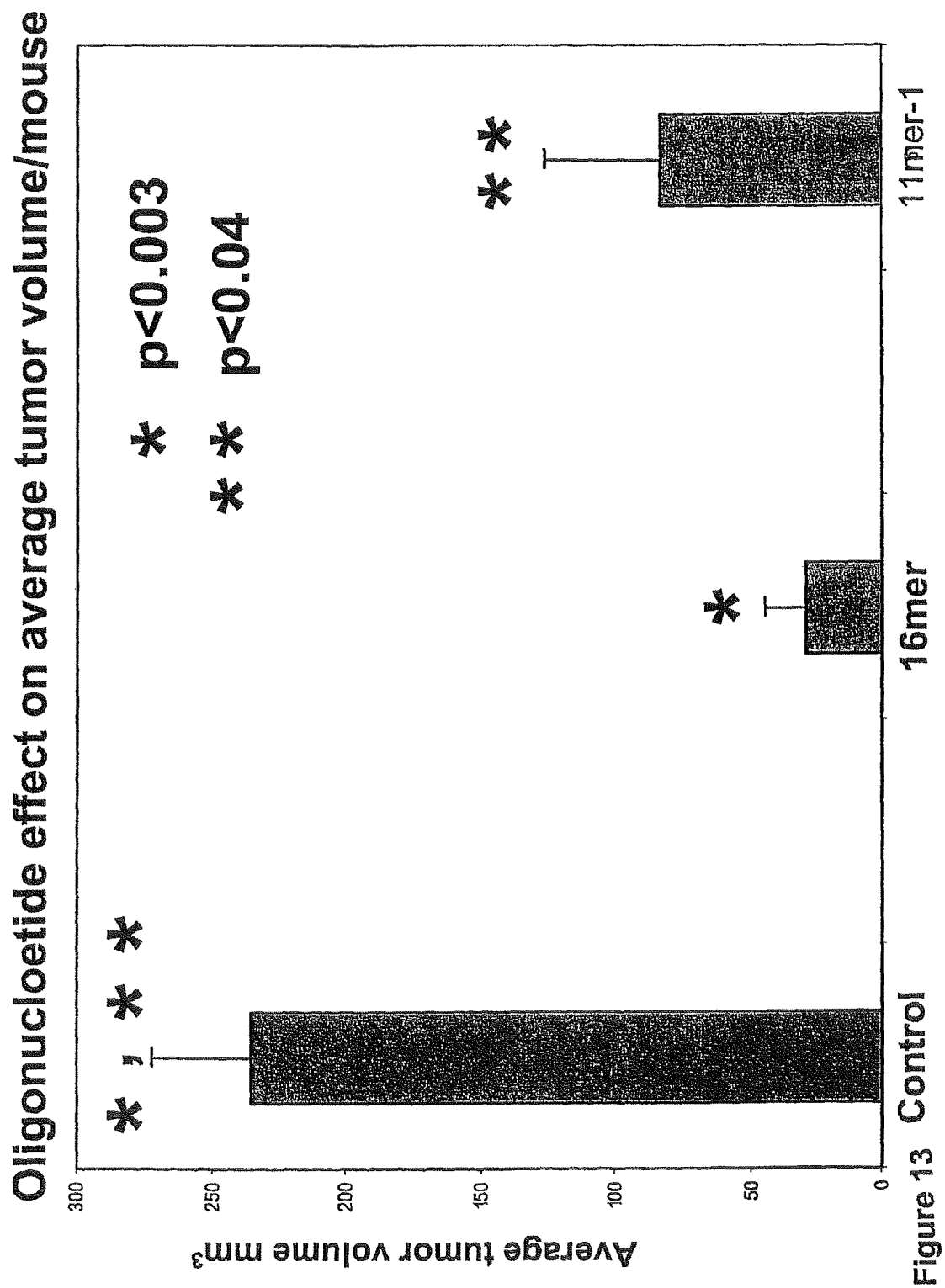
FIG. 13—Effect of oligonucleotides on average tumor volume in SCID mice with MM-AN melanoma.
Figure 14:
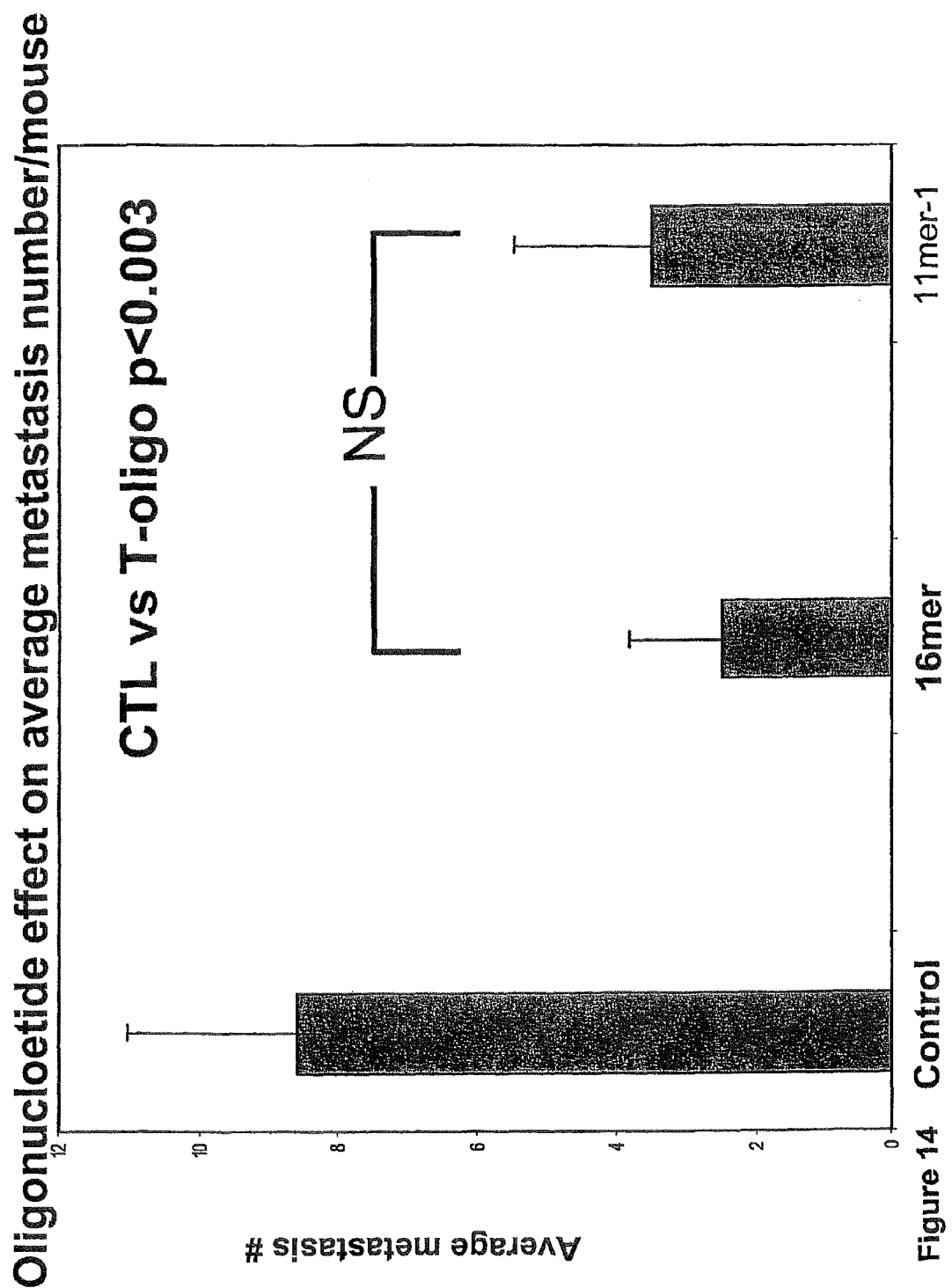
FIG. 14—Effect of oligonucleotides on average metastasis number in SCID mice with MM-AN melanoma.

Experiments were conducted to examine the effect of two T-oligos, an 11mer (pGTTAGGGTTAG) (SEQ ID NO:5) and a 16-mer (pGGTTAGGTGTAGGTTT) (SEQ ID NO:14), compared to control animals. In the first experiment, 2×10$^6$ MM-AN cells were injected subcutaneously into the flank of each animal and on day 5, when tumors were first clinically apparent, the mice received twice daily intravenous injections for 5 days (10 injections) of either the 11-mer (120 nMoles), 16-mer (60 nMoles), or no treatment at all. Results are shown in FIG. 11. Both treatments were quite effective and the half-dose 16-mer was slightly but not statistically superior to the full-dose 11-mer. In a second experiment 2×10$^6$ MM-AN cells were injected into the tail vein, a procedure known to cause widespread metastases, and beginning on day 3 the animals were injected twice daily for 5 days with either the 11-mer or 16-mer or Hank's buffered saline solution (diluent alone) as a control. The experiment was completed when the control group (CTL) began to lose weight and appear ill. The data show that both oligonucleotides were quite effective in reducing number and size of metastases, with the 16-mer at half-dose again slightly more effective than the 11-mer at full-dose and tumor volume (See FIGS. 11-14).

Example 9

Oligonucleotide Killing of Non-Hodgkins Lymphoma Lymphoblasts

The mechanism by which oligonucleotides of the present invention affect cells is partially known. It is known that oligonucleotides activate the ATM kinase, leading to modification of the p95/Nbs1 protein responsible for S-phase arrest of the cell cycle. In the presence of continuous mitogenic stimulation, a $G_1/G_0$ arrest is subsequently achieved, presumably through p53 and p21. Experiments were conducted to extend such studies to ascertain the effects of GTTAGGGT-TAG (SEQ ID NO:2) (referred to hereinafter as T-oligo) on malignant B cell lines (DLCL—diffuse large B-cell lymphoma), wherein the cells were treated with 20 μM of the oligonucleotide followed by FACS analysis as described above.

Rather than a $G_2$/M arrest followed by apoptosis at 48 h, treatment of all cells (40,000) with SEQ ID NO:2 (20 μM) caused a very early S phase arrest, which became a more pronounced by 72 h. All the cell lines behaved with similar kinetics, and cell death was through caspase-3 elevation and apoptosis as before. It is thought that the present T-oligo induces an early S phase arrest largely through phosphorylation of the p95/Nbs1 protein. Apoptotic cells were not a significant fraction of the population until 48 h, when 41% apoptotic cells were observed. After 72 h, 67% of the treated cells were apoptotic. Stabilization of p53 was observed in all cell types tested, but was transient in Toledo cells and MOLT-4 cells, whereas stabilization was sustained in RL and Farage cells. Unlike doxorubicin, T-oligo induced p53 in Toledo cells, indicating that p53 induction was still possible here, but not in MOLT-4, as expected. Taken together with the cell cycle profiles, the evidence clearly supports a conclusion that the apoptotic pathways in the doxorubicin treated cells and T-oligo cases are not the same. The S phase arrest in T-oligo treated DLCL cells is consistent with the arrest seen in MM-AN melanoma cells, but it occurs earlier in DLCL cells; requiring up to 96 h in MM-AN cells and fibroblast-type adherent cells.

Cyclophilin loading controls confirmed equal loading for all cell types, including MOLT-4. A dose-response experiment shows that caspase-3 induction at 4 h after T-oligo exposure (40,000 cells) did not appear to saturate with increasing T-oligo concentration, unlike doxorubicin treated cells. Toledo cells were the most sensitive to T-oligo treatment, showing a steeper dose-response curve, and MOLT-4 the most resistant, suggesting that lack of p53 expression is associated with resistance. It was in some sense surprising that Toledo cells were more sensitive than RL and Farage, because their p53 induction was brief and transient. These differences were consistent with apoptotic cell counts at each time point in each case, although all cell types were killed completely by 96 h. Because oligonucleotides of this size with physiologic phosphodiester linkage have a half-life in culture of 4-6 h, the effective exposure time of DLCL cells to T-oligos in these experiments is probably far less than the 72 h in vitro incubation period shown.

Example 10

Vincristine and T-Oligo Synergistic Killing of DLCL Cells

Three single agents in common use as part of the CHOP+R (cyclophosphamide, doxorubicin, vincristine, prednisone, Rituxin) (Godwin, et al., *Clinical Lymphoma* 2:155-163 (2001) standard of care were tested, in combination with T-oligo described in Example 9: doxorubicin, anti-CD20 and vincristine. We chose doxorubicin because we had already obtained interesting information on its behavior in promoting apoptosis in DLCL cells; and combination with treatment with our oligonucleotide. A purified mouse IgG$_{2b}$,κ monoclonal anti-human CD20 (eBioscience) was used, which is similar to Rituximab, because all the DLCL lines we used were CD20+ and might be susceptible to CD20-receptor mediated apoptosis. Monomeric Rituximab chemosensitizes drug-resistant NHL cells through CD20 signaling, selectively downregulating anti-apoptotic factors, such as Bcl-2, although in patients, there are two other major mechanisms of Rituximab action not seen in tissue culture experiments such as these: complement-mediated cytotoxicity through the $F_c$ portion of the chimeric molecule and antibody-dependent cellular cytotoxicity. We hypothesized that the apoptotic action of anti-CD20 alone might be sufficient to combine with T-oligo apoptotic action. Finally, vincristine was chosen because it too is a component of CHOP, and, like doxorubicin and Rituximab, is likely to work through an apoptotic pathway independent of T-oligo. Vincristine and its Vinca alkaloid sister compound vinblastine are spindle poisons and therefore act as mitotic blockers. In each case, the anticipated mechanistic differences with T-oligo action were hypothesized to create additive or synergistic effects in combination, given the firmly established principle of cancer chemotherapy that multiple, independent modes of drug action are always more effective than single agents or agents that act in the same pathway.

Submaximal concentrations of doxorubicin (50 pM) or anti-CD20 (1 μg/ml) and of T-oligo (2 μM) SEQ ID NO:2 were tested and assayed caspase-3 induction (6000 cells) was assayed, we found that doxorubicin and anti-CD20 did not synergistically induce caspase-3 activity with the T-oligo. In the absence of additional control experiments, we cannot comment further on these negative results. However, assay of caspase-3 activity 12 h after addition of vincristine (25 nM; Sigma) and T-oligo (2 μM) together showed synergistic induction of caspase-3 activity, compared to either single agent. DNA synthesis was measured by BrdU incorporation as detected with FITC anti-BrdU antibody (BD) and correlated with DNA content as detected with 7-aminoactinomycin D fluorescence of fixed cells by flow cytometry (FACS). Untreated control Toledo cells showed normal $G_0/G_1$ phase, S phase and $G_2/M$ phase populations, such as would be expected for proliferating malignant cells, but after 12 hours' treatment with the drug combination were completely devoid of DNA. However, genomic DNA had not yet degraded significantly into the familiar apoptotic pattern, which was indeed observed at later times and correlated with caspase-3 activity. For such low doses of T-oligo and vincristine, we found that caspase-3 induction was best measured at the later time point of 12 h, rather than at 4 h such as we had performed previously, because significant differences were not detectable at 4 h. Furthermore, at higher vincristine concentrations (e.g., 0.25 μM), T-oligo effects were swamped, and again, no differences were detected, due to the high toxicity of vincristine. Observations of BrdU incorporation were consistent with this pattern. It is possible that MOLT-4 cells might show less synergy, given their p53 status, although we have not yet tested these cells. These results suggest that low dose vincristine and low dose T-oligo work well together with minimal side effects in DLCL patients.

Example 11

T-oligo Causes Cell Cycle Arrest of Normal B Cells but not Apoptosis

In order to establish a therapeutic window for the use of T-oligo, either in combination with vincristine or not, it is essential to study its effect on normal cells. All anti-cancer chemotherapeutic drugs are highly toxic and dosages must compromise between efficacy and toxicity. One of the unique reported features of T-oligo is that by mimicking the exposure of telomeric oligonucleotides, the drug activates the sensor responsible for monitoring telomere structure, but the p53-dependent cell cycle arrest that follows is not then followed by apoptosis in normal fibroblasts, the system in which T-oligos (and the thymidine dinucleotides from which T-oligos were deduced) were originally studied. Cell cycle arrest is temporary and, presumably because of the lack of actual DNA damage, cells eventually return to their normal metabolism.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a cancer selected from the group consisting of melanoma, prostate cancer and leukemia in a mammal, said method comprising administering to the mammal an effective amount of a composition comprising an oligonucleotide, said oligonucleotide consisting of GGTTGGTTGGTTGGTT (SEQ ID NO: 29).

2. A method for inhibiting growth of cancer cells selected from the group consisting of melanoma, prostate cancer and leukemia in a human comprising administering to the human an effective amount of a composition comprising an oligonucleotide, said oligonucleotide consisting of GGTTGGTTGGTTGGTT (SEQ ID NO: 29).

* * * * *